United States Patent
Xu et al.

(10) Patent No.: US 10,844,352 B2
(45) Date of Patent: Nov. 24, 2020

(54) COMPOSITIONS AND METHODS FOR THE GENERATION OF MELANOCYTES THROUGH DIRECT REPROGRAMMING

(71) Applicant: THE TRUSTEES OF THE UNIVERSITY OF PENNSYLVANIA, Philadelphia, PA (US)

(72) Inventors: Xiaowei Xu, Monmouth Junction, NJ (US); Ruifeng Yang, Philadelphia, PA (US)

(73) Assignee: The Trustees Of The University of Pennsyivania, Philadelphia, PA (US)

(*) Notice: Subject to any disclaimer, the term of this patent is extended or adjusted under 35 U.S.C. 154(b) by 14 days.

(21) Appl. No.: 15/527,334

(22) PCT Filed: Nov. 18, 2015

(86) PCT No.: PCT/US2015/061290
§ 371 (c)(1),
(2) Date: May 17, 2017

(87) PCT Pub. No.: WO2016/081570
PCT Pub. Date: May 26, 2016

(65) Prior Publication Data
US 2019/0002827 A1    Jan. 3, 2019

Related U.S. Application Data

(60) Provisional application No. 62/081,228, filed on Nov. 18, 2014.

(51) Int. Cl.
| | |
|---|---|
| *C12N 15/00* | (2006.01) |
| *C12N 5/071* | (2010.01) |
| *A61K 35/36* | (2015.01) |
| *A61P 17/00* | (2006.01) |
| *A61L 27/38* | (2006.01) |
| *A61L 27/54* | (2006.01) |
| *A61L 27/58* | (2006.01) |
| *A61L 27/60* | (2006.01) |
| *G01N 33/50* | (2006.01) |

(52) U.S. Cl.
CPC ............ *C12N 5/0626* (2013.01); *A61K 35/36* (2013.01); *A61L 27/3813* (2013.01); *A61L 27/3839* (2013.01); *A61L 27/3886* (2013.01); *A61L 27/3895* (2013.01); *A61L 27/54* (2013.01); *A61L 27/58* (2013.01); *A61L 27/60* (2013.01); *A61P 17/00* (2018.01); *G01N 33/5023* (2013.01); *A61L 2300/64* (2013.01); *A61L 2430/34* (2013.01); *C12N 2501/01* (2013.01); *C12N 2501/115* (2013.01); *C12N 2501/125* (2013.01); *C12N 2501/365* (2013.01); *C12N 2501/60* (2013.01); *C12N 2506/1307* (2013.01); *C12N 2510/00* (2013.01)

(58) Field of Classification Search
CPC .................................................. C12N 5/0626
See application file for complete search history.

(56) References Cited

FOREIGN PATENT DOCUMENTS

| | | |
|---|---|---|
| WO | 2011/104200 A1 | 9/2011 |
| WO | 2014/163206 A1 | 10/2014 |

OTHER PUBLICATIONS

Lang, 2003, Human Molecular Genetics, 12:937-945.*
Lorenz, 2008, Experimental Dermatology, 17:925-932.*
Merrell, 2016, Nat Rev Mol Cell Biol, 17:413-425.*
Heng et al, 2005a, Cell Tissue Res, 321:147-150.*
Heng, 2005b, Biomedicine and Pharmacotherapy59:132-134).*
Bosnali (2008, Biol Chem, 389:851-861).*
Fang (2006, Stem Cells, 24:1668-1677).*
Mica (2013, Cell Reports, 3:1140-1152).*
Ohta (2011, PlosOne, 6Le16182, pp. 1-10).*
Zhou (2009, Cell Stem Cell, 381-384).*
Kim (2009, Cell Stem Cell, 4:472-476).*
Warren et al., "Highly efficient reprogramming to pluripotency and directed differentiation of human cells with synthetic modified mRNA", Cell Stem Cell, 7(5): 618-30 (2010).
Yang et al., "Direct conversion of mouse and human fibroblasts to functional melanocytes by defined factors", Nature Communications, 5: 1-12 (2014).
International Search Report/Written Opinion, dated Mar. 4, 2016, issued in corresponding International Patent Application No. PCT/US2015/061290.
Adameyko, Igor et al., "Sox2 and Mitf cross-regulatory interactions consolidate progenitor and melanocyte lineages in the cranial neural crest", Development, 139: 397-410 (2012).
Baumer, Nicole et al., "Retainal pigmented epithelium determination requires the redundant activities of Pax2 and Pax6", Developmnent, 130: 293-2915 (2003).
Curran, Kevin et al., "Interplay between Foxd3 and Mitf regulates cell fate plasticity in the zebrafish neural crest", Develoment Biology, 344: 107-118 (2010).

(Continued)

*Primary Examiner* — Valarie E Bertoglio
(74) *Attorney, Agent, or Firm* — Kathleen D. Rigaut; Howson & Howson LLP

(57) ABSTRACT

Compositions and methods for generating melanocytes through direct reprogramming are disclosed. Also disclosed are methods of use of such compositions for the treatment of vitiligo and other hypopigmentation disorders. In accordance with the present invention, a method for producing melanocytes suitable for use in human patients is provided. An exemplary method comprises providing cells capable of transdifferentiation into melanocytes, culturing said cells in a chemically defined culture medium, introducing at least two of microphthalmia-associated transcription factor (MITF), SRY-related HMG-box (SOX10) transcription factor and paired box-3 (PAX-3) transcription factor and paired box-3 (PAX-3) transcription factor, or nucleic acids encoding said transcription factors into said cells, wherein expression of said factors induces the cells to transdifferentiae into melanocytes expressing melanocyte markers TYR, DCT, S-100 and Melan-A.

9 Claims, 24 Drawing Sheets

Specification includes a Sequence Listing.

(56) References Cited

OTHER PUBLICATIONS

Du, Pan et al., "lumi: a pipeline for processing illumina microarray", Bioinformatics, 24(13): 1547-1548 (2008).
Galibert, Marie-Dominique et al., "Pax3 and Regulation of the Melanocyte-specific Tyrosinase-related Protein-1 Promoter", The Journal of Biological Chemistry, 274(38): 26894-26900 (1999).
Huang, Pengyu et al., "Induction of functional hepatocyte-like cells from mouse fibroblasts by defined factors", Nature; 475: 386-389 (2011).
Hornyak, Thomas J. et al., "Transcription factors in melanocyte development: distinct roles for Pax-3 and Mitf", Mechanisms of Development, 101: 47-59 (20010.
Collins, Charlotte A. et al., "Reprogramming adult dermis to a neonatal state through epidermal activation of B-catenin", Development, 138: 5189-5199 (2011).
Li, Ling et al., "The Three-Dimensional Human Skin Reconstruct Model: a Tool to Study Normal Skin and Melanoma Progression", JoVE, 54, http://www.jove.com/details.php?id=2937, doi: 10.3791/2937 (2011).
Li, Ling et al., "Human dermal stem cells differentiate into functional epidermal melanocytes", Journal of Cell Science, 123: 853-860 (2009).
Lichti, Ulrike et al., "In Vivo Regulation of Murine Hair Growth: Insights from Grafting Defined Cell Populations onto Nude Mice", J. Invest. Dermatol., 101: 121S-129S (1993).
Mili, Stavroula et al., "Genome-wide screen reveals APC-associated RNAs enriched in cell protrusions", Nature, 453: 115-119 (2008).
Pang, Zhiping P. et al., "Induction of human neuronal cells by defined transcription factors", Nature: 476(7359): 220-223 (2011).
Prince, S. et al., "Stimulation of Melanogenesis by Tetradecanoylphorbol 13-acetate (TPA) in Mouse Melanocytes and Neural Crest Cells", Pigment Cell Res., 16: 26-34 (2003).
Prouty, Stephen M. et al., "Fibroblast-Dependent Induction of a Murine Skin Lesion with Similarity to Human Common Blue Nevus", American Journal of Pathology, 148(6): 1871-1885 (1996).
Qian, Li et al., "In vivo reprogramming of murine cardiac fibroblasts into induced cardiomyocytes", Nature, 485(7400): 593-598 (2012).
Saito, Hideo et al., "Melanocyte-specific Microphthalmia-associated Transcription Factor Isoform Activates Its Own Gene Promoter through Physical Interaction with Lymphoid-enhancing Factor 1*", Jounral of Biological Chemistry, 277(32): 28787-28794 (2002).
Smyth, Gordon K., "Statistical Applications in Genetics and Molecular Biology, Linear Models and Empirical Bayes Methods for Assessing Differential Expression in Microarray Experiments", Article 3, 2004.
Song, Kunhua et al., "Heart repair by reprogramming non-myocytes with cardiac transcription factors", Nature, 485(7400): 599-604 (2012).
Southard-Smith, E. Michelle et al., "Sox10 mutation disrupts neural crest development in Dom Hirschsprung mouse model", Nature Genetics, 18: 60-64 (1998).
Subramanian, Aravind et al., "Gene set enrichment analysis: A knowledge-based approach for ingterpreting genome-wide expression profiles", PNAS, 102(43): 15545-15550 (2005).
Tropepe, Vincent et al., "Retinal Stem Cells in the Adult Mammalian Eye", Science, 287: 2032-2036 (2000).
Weinberg, Wendy C. et al., "Reconstitution of Flair Follicle Development In Vivo: Determination of Follicle Formation, Hair Growth, and Hair Quality by Dermal Cells", J. Invest. Dermatol., 100: 229-236 (1993).
Zheng, Ying et al., "Mature Hair Follicles Generated from Dissociated Cells: A Universal Mechanism of Folliculoneogenesis", Developmental Dynamics, 239: 2619-2626 (2010).
Zheng, Ying et al., "Organogenesis from Dissociated Cells: Generation of Mature Cycling Hair Follicles from Skin-Derived Cells", J. Invest. Dermatol., 124: 867-876 (2005).
Dankort, David et al., "BrafV600E cooperates with Pten loss to induce metastatic melanoma", Nature Genetics, 41: 544-552 (2009).
Morris, Rebecca J. et al., "Capturing and profiling adult hair follicle stem cells", Nature Biotechnology, 22(4): 411-417 (2004).
Sviderskaya, Elena V. et al., "Complementation of Hypopigmentation in p-Mutant (Pink-Eyed Dilution) Mouse Melanocytes by Normal Human P cDNA, and Defective Complementation by OCA2 Mutant Sequences", J. Invest. Dermatol., 108: 30-34 (1997).
Benjamini, Yoav et al., "Controlling the False Discovery Rate: A Practical and Powerful Approach to Multiple Testing", J. R. Statist. Soc. B, 57(1): 289-300 (1995).
Vierbuchen, Thomas et al., "Direct conversion of fibroblasts to functional neurons by defined factors", Nature, 25: 463(7284): 1035-1041 (2010).
Pfisterer, Ulrich et al., "Direct conversion of human fibroblasts to dopaminergic neurons", PNAS, 108(25): 10343-10348 (2011).
Sekiya, Sayaka et al., "Direct conversion of mouse fibroblasts to hepatocyte-like cells by defined factors", Nature, 475: 390-393 (2011).
Caiazzo, Massimiliano et al., "Direct generation of functional dopaminergic neurons from mouse and human fibroblasts", Nature, 476: 224-227 (2011).
Ieda, Masaki et al., "Direct Reprogramming of Fibroblasts into Functional Cardiomyocytes by Defined Factors", Cell, 142: 375-386 (2010).
Tachibana, Masayoshi et al., "Ectopic expression of MITF, a gene for Waardenburg syndrome type 2, converts fibroblasts to cells with melanocyte characteristics", Nature Genetics, 14: 50-54 (1996).

* cited by examiner

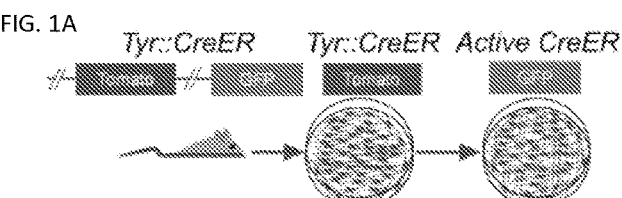
FIG. 1A
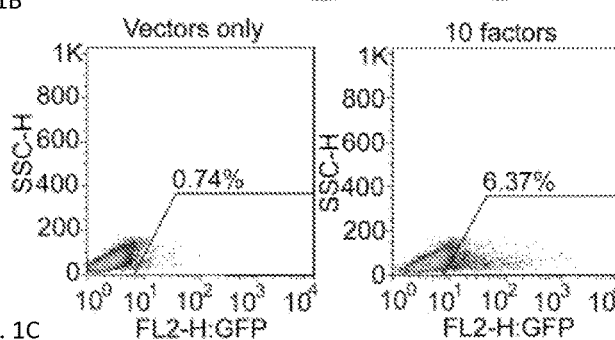
FIG. 1B
FIG. 1C
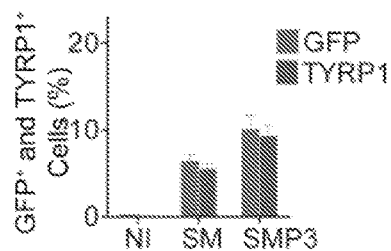
FIG. 1D
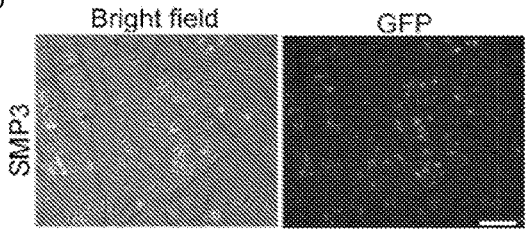
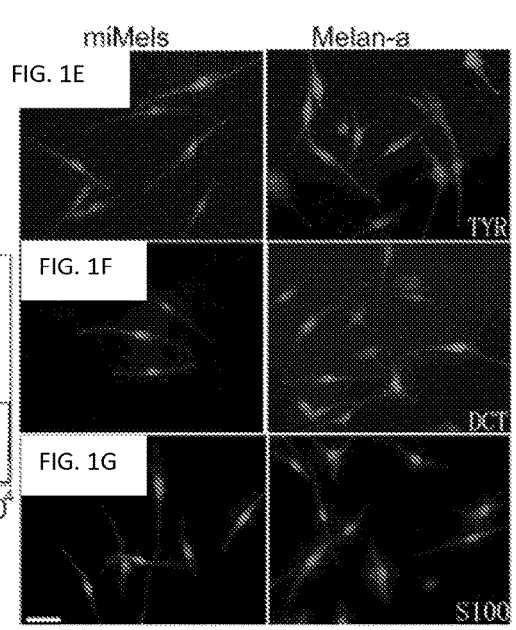
FIG. 1E
FIG. 1F
FIG. 1G
FIG. 1H
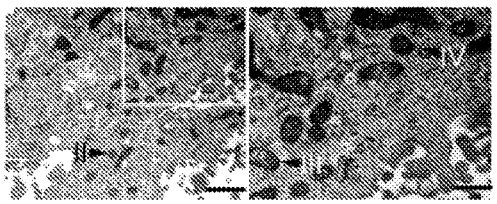

FIG. 15A
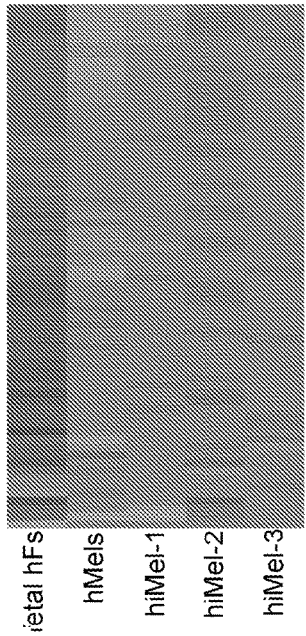
FIG. 15B
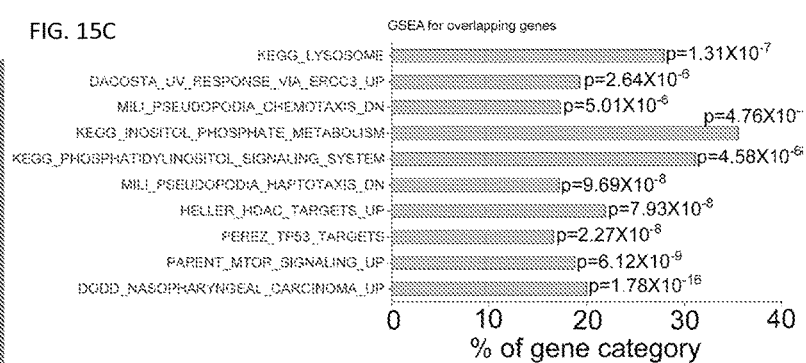
FIG. 15C
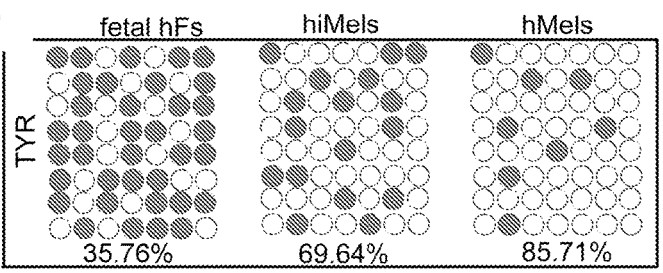
FIG. 15D
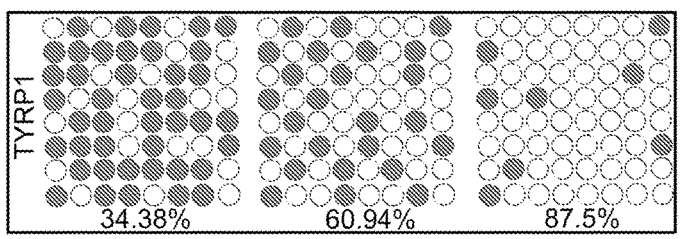
FIG. 15E
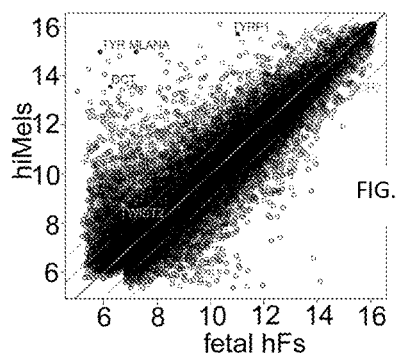
FIG. 15F
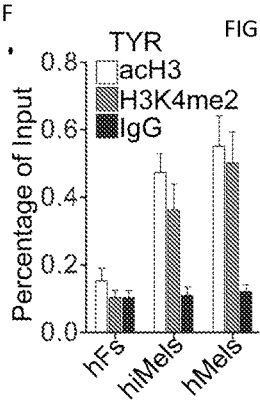
FIG. 15G
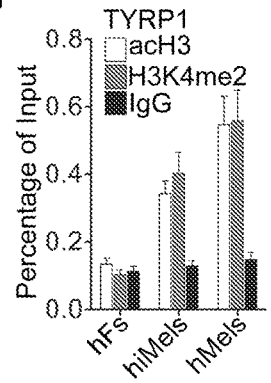

SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gctggaaatg ctagaataca g                                         21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ttccaggctg atgatgtcat c                                         21

```
<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
atggttgcgt ctctaagatc ctg                                            23

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gcgtccttga gcaatttgtc                                                20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ttcaggctca ctacaagagt g                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tcagagatgg cagtgtagag g                                              21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
cttcttctcc tcctggcaga tc                                             22

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tgggggtttt ggctttgtc                                                 19

<210> SEQ ID NO 9
<211> LENGTH: 24
<212> TYPE: DNA
<213> ORGANISM: Artificial Sequence
<220> FEATURE:
<223> OTHER INFORMATION: Primer
```

```
<400> SEQUENCE: 9
gccccaactc tgtctttcct caat                                              24

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
gatcggcgtt atacctcctt agc                                               23

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ggaccggccc cgactgtaat c                                                 21

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
gtagggcaac gcaaaggact cat                                               23

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
actgcaactg ggtcctgcaa c                                                 21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tggcagcaag aacacaatcc a                                                 21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
atgcgcctag agaacaaaga c                                                 21

<210> SEQ ID NO 16
<211> LENGTH: 20
```

-continued

<212> TYPE: DNA
<213> ORGANISM: Artificial Sequence
<220> FEATURE:
<223> OTHER INFORMATION: Primer

<400> SEQUENCE: 16
tagcaggttt gacggtcagc                                                    20

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
cgtgaccctt tctcctgtaa g                                                  21

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ttataaaatg gaaagggtta gt                                                 22

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
tccagcagca aagccccag                                                     19

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
gtgagcaggc ccttctcagg t                                                  21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
aataggagac aaaggagagt g                                                  21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
cttaaaatgt tgcatttgtc t                                              21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
cagcccagca tcattcttct c                                              21

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
ggattacgcc gtaaaggtcc ctc                                            23

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
cctgcgtctg gagaaagac                                                 19

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ggatcccatc aagtcatccg tg                                             22

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tctgttagag atacattatt ag                                             22

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gactcattgc caatgagtcg ct                                             22

<210> SEQ ID NO 29
<211> LENGTH: 21
<212> TYPE: DNA
<213> ORGANISM: Artificial Sequence

```
<220> FEATURE:
<223> OTHER INFORMATION: Primer

<400> SEQUENCE: 29
ccagagactt gactgctgga g                                              21

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
tgcccatctg gcaatacct                                                 19

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
cattcctcac aaaagggag                                                 19

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32 cgtgacccttt tctcctgtaa g                                             21

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
tctgggctct gaagacaatc t                                              21

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
cagttaatag actacaaaac taat                                           24

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
aaatataaga tcttatcatc ag                                             22
```

```
<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
ttttattctg ttattcaact gtt                                              23

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
taacgtgaga tatccccaca atg                                              23

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
tatcacatgt cttggctgag ac                                               22

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
catttccaat ttggatgctc t                                                21

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
taagtgcatg tggattgctg                                                  20
```

COMPOSITIONS AND METHODS FOR THE GENERATION OF MELANOCYTES THROUGH DIRECT REPROGRAMMING

CROSS REFERENCE TO RELATED APPLICATION

This application is a § 371 of International Application No. PCT/US2015/061290, filed Nov. 18, 2015, which claims priority to U.S. Provisional Application No. 62/081,228 filed Nov. 18, 2014. The entire disclosure of each of the aforesaid applications is incorporated by reference in the present application.

STATEMENT OF RIGHTS TO INVENTIONS MADE UNDER FEDERALLY SPONSORED RESEARCH

This invention was made with government support under grant number AR054593 awarded by the National Institutes of Health. The government has certain rights in the invention.

FIELD OF THE INVENTION

This invention relates to the fields of molecular biology and production of human melanocytes. More specifically, the invention provides compositions and methods for transdifferentiating human fibroblasts directly into melanocytes.

BACKGROUND OF THE INVENTION

Numerous publications and patent documents, including both published applications and issued patents, are cited throughout the specification in order to describe the state of the art to which this invention pertains. Each of these citations is incorporated herein by reference as though set forth in full.

Melanocytes play a critical role in protecting human skin from harmful ultraviolet (UV) rays. Defects in melanocytes can lead to a number of pigmentation disorders and skin cancers such as piebaldism, albinism, vitiligo, hair graying and melanoma. Vitiligo is a skin condition resulting from loss of melanocytes in the skin. As a result, white patches of skin appear on different parts of the body. Any part of the body may be affected. In the United States, 2 to 5 million people have the disorder and about 1 to 2 percent of the world's population is affected by this disease. It affects people of both sexes equally, and it affects all races. It can begin at any age, though about fifty percent of people with vitiligo develop it before the age of twenty five. Vitiligo can cause extreme distress to sufferers because of its unusual appearance.

There are a number of treatment options. Many treatments can have unwanted side effects. Treatments can take a long time, and sometimes they don't work. Current treatment options for vitiligo include medical, surgical, and other treatments. Most treatments are aimed at restoring color to the white patches of skin. Medical treatment includes steroid creams with or without ultraviolet A (UVA) light (PUVA). Surgical treatment includes skin grafts from a person's own tissues or autologous melanocytes transfer. The doctor takes skin from one area of a patient's body and attaches it to another area, or isolate melanocytes from the skin and transfer to the affected area. However, the efficacy of treatment is limited by the difficulty in generating sufficient numbers of autologous melanocytes as adult melanocytes have very limited proliferation capacity.

Despite years of research efforts, effective therapies for vitiligo are not yet available. Clearly, a need exists for the development of such therapies.

SUMMARY OF THE INVENTION

In accordance with the present invention, a method for producing melanocytes suitable for use in human patients is provided. An exemplary method comprises providing cells capable of transdifferentiation into melanocytes, culturing said cells in a chemically defined culture medium, introducing at least two of microphthalmia-associated transcription factor (MITF), SRY-related HMG-box (SOX10) transcription factor and paired box-3 (PAX-3) transcription factor, or nucleic acids encoding said transcription factors into said cells, wherein expression of said factors induces the cells to transdifferentiae into melanocytes expressing melanocyte markers TYR, DCT, S-100 and Melan-A. The method optionally entails isolating the melanocytes. In one approach, two transcription factors, MITF and SOX10 are introduced. In a preferred embodiment, all three transcription factors are introduced. The cells are preferably mammalian in origin. Particularly preferred are fibroblast cells.

The transcription factors may be encoded by one or more expression vectors, or the proteins encoded thereby introduced directly into cells. Alternatively, synthetic mRNA may be employed to introduce the transcription factors into recipient cells. Isolated melanocytes so produced also form an aspect of the invention.

In another aspect, the invention provides a method for delivering melanocytes to a patient in need thereof for a variety of medical conditions. An exemplary method comprises providing autologous cells from said patient, said cells being capable of transdifferentiation into melanocyte, preparing melanocytes from these cells as described above, harvesting the melanocytes, and introducing melanocytes into said patient, said melanocytes expressing melanocyte specific markers and producing pigment. In one approach, the introducing step comprises removing epidermis from an affected area, thereby creating a treatment site, and applying a composition comprising the isolated melanocytes, and optionally keratinocytes directly onto said treatment site. A biocompatible membrane may also be utilized to facilitate engraftment of said cells. The foregoing method can be used to advantage for the treatment of conditions which include, without limitation, piebaldism, albinism, vitiligo, and hair graying.

Finally, the invention also provides a method for identifying agents which modulate melanocyte viability or function. In one embodiment the method comprises providing melanocytes prepared as described above, incubating the cells in the presence and absence of a test agent and analyzing whether said agent alters a cellular parameter associated with melanocyte viability or function, thereby identifying agents which alter said parameter. Parameters to be altered include for example, cell viability, melanocyte marker expression and pigment production. In another aspect, the agent inhibits malignant transformation of said melanocytes following exposure to UV irradiation.

BRIEF DESCRIPTION OF THE DRAWINGS

FIGS. 1A-1H. Screening for melanocyte direct reprogramming factors. FIG. 1A. Scheme for melanocyte direct reprogramming transcription factor (TF) screening. Screening was performed using fibroblasts from the Tyrosinase-CreER/Gt(ROSA)26Sor$^{tm4(ACTB-tdTomato-EGFP)Luo}$/J mice. When tyrosinase (TYR) was activated, Cre activation resulted in excision of the tomato cassette and expression of GFP in the presence of 4-HT. FIG. 1B. Flow cytometric analysis of the GFP+ cells after cells were infected with virus packaged with 10 candidate factors (right panel) or vector only (left panel). FIG. 1C. GFP and TYRP1 expression by flow cytometry analysis after infection with control vectors (NI), Sox10 and MITF (SM) or Sox10, MITF and Pax3 (SMP3). Representative data are from three independent experiments. FIG. 1D. Morphology of GFP+ cells after sorting. Mouse fibroblasts were infected with SMP3 and sorted based on GFP expression at Day 14. Scale bar indicates 50 μm. FIGS. 1E-1G. Immunostaining analysis of induced mouse melanocytes (miMels) using antibodies specific for TYR (FIG. 1E), DCT (FIG. 1F) and S100 (FIG. 1G). Secondary antibody was labeled with Alexa Fluro 594. DAPI was used to stain the nuclei. Melan-a mouse melanocytes were used as a positive control. Scale bar indicates 30 μm. FIG. 1H. Electron microscopy analysis showed that miMels contained many mature melanosomes in the cytoplasm. Arrow heads point to the different stages of melanosomes, including stage II, III and IV. Scale bar indicates 400 nm.

FIG. 8A. Immunocytochemical staining of iMels. TTFs derived from Tyrosinase-CreER/Gt(ROSA) 26Sor$^{tm4(ACTB-tdTomato-EGFP)Luo}$/J mice were reprogrammed by SMP3. After direct reprogramming, iMels were stained with antibodies specific for SILV or Melan-A. Melan-a mouse melanocytes were used as a positive control. Scale bar, 30 μm. FIG. 8B. qRT-PCR analysis of melanocyte specific markers, such as TYR, TYRPLOCT and SILV, and endogenous expression of SOX10, MITF and PAX3 in TTFs infected with viruses packaged with vector only (NI), SM and SMP3. Melan-a mouse melanocytes were used as a positive control. Data shown are mean±SD of the expression from three independent experiments. FIG. 8C. qRT-PCR analysis of transgenic and endogenous SOX10, MITF and PAX3 expression in SMP3 infected TTFs. Data shown are mean±SD of the expression from three independent experiments.

FIG. 9A. RT-PCR analysis of melanocytic markers in MEFs that were reprogrammed using SMP3. MEFs infected with SMP3 were collected for RT-PCR analysis at Day 5 after infection. MEFs and melan-a mouse melanocytes were used as negative and positive controls, respectively. The markers included TYR, TYRP1, OCT, MITF (endo), SOX10 and PAX3. GAPDH here was used as an internal control. FIG. 9B. Morphologies of parental MEFs and SMP3 induced MEFs (SMP3-MEFs). MEFs (left panel) were infected with viruses containing SMP3, cultured for 19 days and then selected under G418 and photographed (middle panel). The cells were then stained by Dopamine and showed Dopa activity (right panel). Scale bar, 50 μm.

FIG. 10A. lmmunocytochemical staining of iMels derived from MEFs (MEF-iMels) using antibodies specific for TYR, S100 and Melan-A. Scale bar, 25 μm. FIG. 10B. qRT-PCR analysis of melanocyte markers, including MITF(endo), TYR, TYRP1, OCT, P, SOX10(endo) and PAX3(endo) in MEF-iMels and MEFs. Data shown are mean±SD of the expression from three independent experiments.

FIGS. 11A-11D. RT-PCR analysis of melanocyte markers in TTFs after infection with different combinations of transcription factors. FIG. 11A. Adult TTFs from C57B6 mice were infected with different combinations of SOX10 (S), MITFGFP (MGFP) and PAX3 (P3). TTFs were collected for RT-PCR analysis at Day 5 after infection. FIG. 1A. Morphologies of TTFs and SMGFPP3 infected TTFs. TTFs were infected with viruses carrying SOX10/MITFGFP/PAX3 (SMGFPP3), cultured for 21 days and photographed (FIG. 11B). TTF culture was used as a negative control (FIG. 11B). Scale bar, 50 μm. GFP+ cells were sorted out and cultured for additional 14 days. These cells showed typical melanocyte morphology and pigmentation (FIG. 11C). Arrow heads point to pigmentation. Scale bar in upper panels, 50 μm; Scale bar in lower panels, 25 μm. FIG. 11D. qRT-PCR analyses of the melanocyte markers in TTFs and iMels derived from TTFs (TTF-iMels). MITF (endo), TYR, TYRP1, DCT, P, SOX10 (endo) and PAX3 (endo) were analyzed in TTFs and iMels derived from TTFs. Data shown are mean±SD of the expression from three independent experiments.

FIG. 12B. Cell morphology of fetal hFs and induced melanocytes derived from fetal hFs. Representative images of fetal hFs and induced melanocytes derived from fetal hFs (fetal hF-SMGFPP3) at Day 40. Scale bar indicates 50 µm. FIGS. 12C-12F. Immunostaining analysis of human induced melanocytes (hiMels) derived from fetal hFs and normal human skin melanocytes (hMels) using antibodies specific for TYR(FIG. 12C), TYRP1 (FIG. 12D), DCT (FIG. 12E) and SILV (FIG. 12F). The secondary antibody was labeled with Alexa Fluro 594. DAPI was used to stain the nuclear DNA. Scale bar indicates 20 µm. g. qRT-PCR analysis of melanocytic specific markers, such as TYR, TYRP1, DCT and SILV, and endogenous expression of SOX10, MITF and PAX3 in fetal hFs infected with vector virus only (NI), SMGFP and SMGFPP3 and hMels. Data shown are mean±SD of the expression from three independent experiments. FIG. 12H. Fontana-Masson staining showed melanin pigment in hiMels. Scale bar in left panel indicates 25 µm and scale bar in right panel indicates 10 µm. Arrow heads point to the melanin pigment. FIG. 12I. Electron microscopy images of hiMels with many mature melanosomes in the cytoplasm. II: stage II melanosome; III: stage III melanosome; IV: stage IV melanosome. Scale bars indicate 1 µm in left panel and 400 nm in right panel. Arrow heads point to melanosomes.

FIG. 13A. Representative flow cytometry plots for analyses of TYR+ and TYRP+ cells after reprogramming with SMGFPP3 at indicated time points. Fetal hFs were infected with SMGFPP3, sorted and selected in the medium containing G418. Cells were collected and flow cytometrically analyzed at Day 0, 40 and 80. FIG. 13B. Representative flow cytometry plots for analyses of TYR+ cells after reprogramming with SMGFPP3. FIG. 13C. Immunocytochemical analysis of S100 and Melan-A in normal skin melanocytes (hMels) and iMels derived from fetal hFs (hiMels). Scale bar, 25 µm. FIG. 13D. qRT-PCR analysis of transgenic and endogenous (Endo) expression of human PAX3 (hPAX3), human SOX10 (hSXO10) and human MITF (hMITF) in hiMels. Data shown are mean±SD of the expression from three independent experiments.

FIG. 14A. qRT-PCR analysis of the trangene expression of SOX10, MITF and PAX3 in the presence or absence of Doxycycline (DOX). FIG. 14B. qRT-PCR analysis of melanocytic markers in hiMels with DOX withdrawn 14 days after induction (DOX withdrawn), hiMels with DOX persistence presence of DOX (DOX). hMels and fetal hFs (hFs) were used as positive and negative controls, respectively. Data shown are mean±SD of the expression from three independent experiments. FIG. 14C. Immunostaining analysis of melanocytic markers including TYR, OCT, TYRP1 and S100 in hiMeis with DOX withdrawn 14 days after induction. Scale bar, 30 µm.

FIGS. 15A-15G. Molecular characterization of induced human melanocytes. FIG. 15A. Heat-map of genes differentially expressed in RNA-microarray analysis performed on human fetal fibroblasts (fetal hFs), induced melanocytes derived from human fetal fibroblast (hiMels) and normal skin melanocytes (hMels). FIG. 15B. Scatter plots show that melanocytic markers are expressed in hiMels, but not in fetal hFs. FIG. 15C. Gene Set Enrichment Analysis for the overlapping genes between hMels and hiMels. Many gene sets including KEGG_LYSOSOME, DACOSTA_UV_RESPONSE_VIA_ERCC3, PARENT_MTOR_SIGNALING_UP, MILI_PSEUDOPODIA_HAPTOTAXIS_DN and MILI_PSEUDOPODIA_CHEMOTAXIS_DN were enriched in hiMels and hMels. FIG. 15D and FIG. 15E. DNA methylation analysis of the promoters of TYR (FIG. 15D) and TYRP1 (FIG. 15E) in fetal hFs, hiMels and hMels. Open circles indicate unmethylated CpG dinucleotides, while closed circles indicate methylated CpGs. FIG. 15F and FIG. 15G. Histone modification analysis of promoters of TYR and TYRP1 in fetal hFs, hiMels and hMels. Chromatin immunoprecipitation was performed using antibodies against dimethylated histone H3K4 (H3K4me2) and H3 acetylation (acH3). TYR and TYRP1 promoters showed enrichment for the active states (H3K4 me2 and acH3) in hiMels, similar to hMels. In fetal hFs, TYR and TYRP1 promoters appeared in the inactive state. Representative data are from three independent experiments.

FIG. 16A. Sphere formation capacity of the Passage 0 (PO), Passage 1 (P1) and Passage 2 (P2) human fetal primary fibroblasts (Fetal hFs) isolated from fetal skin. FIG. 16B. Sphere formation capacity of PDGFRA+/c-Kit fibroblasts from primary fetal fibroblasts. PO fibroblasts were MACS microbeads purification using an antibody against PDGFRA (positive selection) and c-Kit (negative selection). PDGFRA+/c-Kif fibroblasts were used in the sphere formation assays. PO indicates Passage 0, P1 indicates Passage 1 and P2 indicates Passage 2. Representative data are from three independent experiments.

FIG. 17A. Immunocytochemical staining analysis of TYR, OCT and Melan-A in fetal hFs. Fetal hFs were negative for these markers. Scale bar, 25 µm. FIG. 17B. Flow cytometric analysis of the percentage of TYR+ and TYRP1+ cells in the fibroblasts. Representative results are from 3 independent experiments.

FIG. 18A. Flow cytometric analysis of the percentage of PDGFRA+ and c-Kit+ cells in primary human fetal fibroblasts. Representative data are from 3 independent experiments. FIG. 18B. qRT-PCR analysis of melanocytic markers in hMels, hiMels derived from human fetal PDGFRA+/c-Kif fibroblasts (hiMels) and human fetal PDGFRA+/c-Kif fibroblasts (hFs). Data shown are mean±SD of the expression from three independent experiments. FIG. 18C. lmmunostaining analysis of melanocytic markers in hiMels. Scale bar, 30 µm.

FIGS. 21A-21F. Functional analysis of induced human melanocytes in vivo. FIG. 21A. The skin reconstitution assays showed pigmented hair follicles using hiMels. hiMels, hMels or fetal hFs combined with neonatal mouse dermal fibroblasts and epithelial cells derived from BALB/c (albino) mouse skin. Cells were injected into the back skin of an immunodeficient mouse. After 3 weeks, grafts were photographed from the underside of the skin. Pigmented hair follicles were observed in the reconstitution assays using hiMels or hMels; whereas pigmented hair follicles were not observed using fetal hFs. Scale bar, 5 mm. Representative images from 5 mice. FIG. 21B. Human-specific Alu staining (green nuclei) confirmed human origin of iMels (left, up panel) and H&E staining of consecutive section showed a cyst with hair follicle formation (right, upper panel); Scale bar, 200 µm. Human cells located in the bulb region of a hair follicle (left, lower panel) and basal layer of epidermis (right, lower panel); Scale bar, 50 µm.

FIG. 21C and FIG. 21D. Immunostaining of the xenografts from the patch assays using antibodies against human DCT (FIG. 21C) and TYRP1 (FIG. 21D). DCT+ cells were present in the interfollicular dermis and bulb region of hair follicles. TYRP1+ cells were observed in both hair follicles and the epidermis. Scale bar, 20 µm. FIG. 21E. Immunohistochemical staining of the xenografts using antibodies against human S100. S100+ positive cells were located in epidermis, hair follicle and the dermis. Scale bar, 20 µm. FIG. 21F. Fontana-Masson staining of the xenografts showed no pigment in xenografts formed by fetal hFs and mouse cells (left); whereas abundant melanin pigment was evident in the epidermis and follicular epithelium when hiMels were included in the assays (right). Scale bar, 20 µm.

FIG. 22A. White hair follicles and hair shafts were observed at the site of injection, and photographed from the underside of the skin. Arrowheads point to the hair shafts. Scale bar, 2 mm. FIG. 22B. Fantana-Mason staining of the reconstructed skin did not show any pigment in the hair follicle or epidermis. Scale bar, 50 µm.

FIG. 21A. Adult hFs were reprogrammed using SMGFPP3 and stained for TYR, OCT, S100 and Melan-A expression. Scale bar, 30 µm. FIG. 21B. Quantification of TYR+ and OCT+ cells by immunostaining analysis as described in a. Representative data are from three independent experiments.

DETAILED DESCRIPTION OF THE INVENTION

Figure 2:
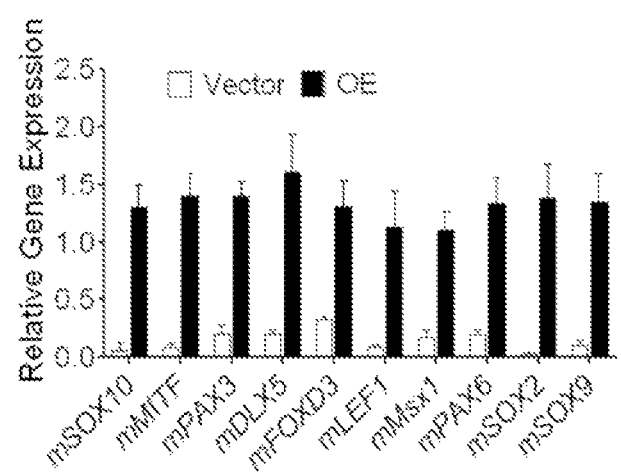
FIG. 2. qRT-PCR analysis of candidate factor expression. SOX2, MITF, PAX3, DLX5, FOXD3, LEF1, MSX1, PAX6, SOX2 and SOX9 expression in fibroblasts after infection. mSOX2, mMITF, mPAX3, mDLX5, mFOXD3, mLEF1, mMSX1, mPAX6, mSOX2 and mSOX9 mean these genes are mouse origin. OE represents fibroblasts infected with candidate factors; vector represents fibroblasts infected with empty vectors. Data shown are mean±SD of the expression from three independent experiments.

Lineage-specific transcription factors induce cell-fate changes in somatic cells by directly reprogramming them to an alternative differentiated fate without transitioning through an induced pluripotent stem cell (iPSCs) state (1-8). Direct reprogramming provides a fundamentally new approach for the generation of patient-specific cells. Here, by screening a pool of candidate transcription factors, we identified a combination of three factors, MITF, SOX10 and PAX3, that directly convert mouse and human fibroblasts to functional melanocytes. Induced melanocytes (iMels) activated melanocyte-specific networks, expressed the components of pigment production and delivery, and produced melanosomes. Human iMels properly integrated into the dermal-epidermal junction and produced and delivered melanin pigment to surrounding keratinocytes in a 3D organotypic skin reconstruction. Human iMels generated pigmented epidermis and hair follicles in skin reconstitution assays in vivo. The generation of iMels has important implications for studies of melanocyte lineage commitment, pigmentation disorders, and cell replacement therapies.

DEFINITIONS

With reference to nucleic acids of the invention, the term "isolated nucleic acid" is sometimes used. This term, when applied to DNA, refers to a DNA molecule that is separated from sequences with which it is immediately contiguous (in the 5' and 3' direction) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

The term "promoter region or expression control sequence" refers to the transcriptional regulatory regions of a gene, which may be found at the 5' or 3' side of the coding region, or within the coding region, or within introns. Such sequences regulate expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc.

Those skilled in the art will recognize that a nucleic acid vector can contain nucleic acid elements other than the promoter element and the nucleic acid molecule of interest. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

In some embodiments, the expression control sequence comprises a tissue- or organ-specific promoter. Many such expression control sequences will be evident to the skilled worker.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, a viral vector, a naked plasmid and the like.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

Polymerase chain reaction (PCR) has been described in U.S. Pat. Nos. 4,683,195, 4,800,195, and 4,965,188, the entire disclosures of which are incorporated by reference herein. The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

A "clonal cell population" refers to a group of identical cells that are derived from the same cell.

"Fibroblasts" can be obtained from many sources which include, without limitation, human adult fibroblasts, human fetal fibroblasts (which may be obtained from the same or a different tissue source from which the keratinocytes are obtained), human fetal skin fibroblasts and fibroblast stem cells. In a preferred embodiment of the invention, the fibroblasts and keratinocytes will be obtained from the same tissue source. The phrase "activated fibroblast" is used to refer to fibroblasts that are induced during tumor invasion.

"Multipotent" implies that a cell is capable, through its progeny, of giving rise to several different cell types found in the adult animal.

"Pluripotent" implies that a cell is capable, through its progeny, of giving rise to all the cell types which comprise the adult animal including the germ cells. Both embryonic stem and embryonic germ cells are pluripotent cells under this definition.

The term "cell line" as used herein can refer to cultured cells that can be passaged at least one time without terminating. The invention relates to cell lines that can be passaged at least 1, 2, 5, 10, 15, 20, 30, 40, 50, 60, 80, 100, and 200 times. Cell passaging is defined hereafter.

The term "suspension" as used herein can refer to cell culture conditions in which cells are not attached to a solid support. Cells proliferating in suspension can be stirred while proliferating using apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the invention can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel which has been supplemented with medium suitable for further cell proliferation.

The term "proliferation" as used herein in reference to cells can refer to a group of cells that can increase in number over a period of time.

The term "reprogramming" or "reprogrammed" as used herein can refer to materials and methods that can convert a cell into another cell having at least one differing characteristic. Also, such materials and methods may reprogram or convert a cell into another cell type that is not typically expressed during the life cycle of the former cell. For example, (1) a non-totipotent cell can be reprogrammed into a totipotent cell or (2) a precursor cell can be reprogrammed into a totipotent cell.

The term "differentiated cell" as used herein can refer to a precursor cell that has developed from an unspecialized phenotype to a specialized phenotype. For example, embryonic cells can differentiate into an epithelial cell lining the intestine. Materials and methods of the invention can reprogram differentiated cells into totipotent cells. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

The following materials and methods are provided to facilitate the practice of the present invention.

Cell Culture

TTFs were isolated from the Tyrosinase-CreER/Gt (ROSA) $26Sor^{tm4(ACTB-tdTomato-EGFP)Luo}$/J transgenic and C57BL/6 mice. Tails were peeled, minced into 1 cm pieces, placed on culture dishes, and incubated in MEF media (Dulbecco's modified Eagle medium (DMEM; Invitrogen) containing 10% fetal bovine serum (FBS; Hyclone), non-essential amino acids (Invitrogen), sodium pyruvate and penicillin/streptomycin (Invitrogen)) for 5 days. MEFs were isolated from Day 14.5 mouse embryos. Cells were split no more than three times in all experiments. Human fetal fibroblasts were isolated from 20-week old fetal skin (Advanced Bioscience Resources, Inc; Alameda, Calif.). Human adult fibroblasts were obtained from discarded normal skin after surgery following a protocol approved by the University of Pennsylvania Institutional Review Board. Human skin samples were mechanically dissociated, plated on gelatin-coated dishes and cultured in MEF media. XB2, an immortal line of mouse keratinocytes, was culture in MEF media. HEK 293T cells and human fibroblasts were cultured in DMEM supplemented with 10% fetal bovine serum (FBS), 2 mM L-glutamine, 100 unit/ml penicillin and 100 µg/ml of streptomycin (all from Invitrogen).

Viral Infection

For mouse cell infection, the viruses were packaged by transfecting retroviruses and pECO into 293T cells. For human cell infection, the pantropic viruses were packaged by transfecting the retrovirus vectors, pUMVC and pCMV-VSVG into 293T cells. To improve the pantropic retrovirus infection efficiency, we concentrated the virus using the Retro-X™ Concentrator (Clontech) according to manufacturer's instructions. After 48 h, growth medium was replaced with mouse melanocyte inducing medium containing RPMI 1640 (Invitrogen), 10% FBS, 10 ng/ml bFGF (Invitrogen), 100 ng/ml SCF (R&D), 100 nM ET-3 (American Peptide Company), 20 pM cholera toxin (CT) (Sigma-Aldrich) and 200 nM 12-O-tetradecanoyl-phorbel 13-acetate (TPA) (Sigma-Aldrich). Human melanocyte inducing medium contained medium 254, 10 ng/ml bFGF, 100 ng/ml SCF, 100 nM ET-3. For G418 selection, 60 ug/mL G418 was added in melanocyte induction media.

Flow Cytometry and Cell Sorting

Cells ($2.5 \times 10^6$ cells/ml) were stained with antibodies against TYR (Abcam), TYRP1 (Sigma), c-Kit (eBioscience) and PDGFRA (BioLegend). To detect intracellular proteins, staining was carried out on cells fixed with 4% paraformaldehyde (Electron Microscopy Sciences) in PBS. Staining was performed in PBS with 2% FBS. Stained cells and GFP+ cells were analyzed using an LSRII flow cytometer (BD). For FACS sorting, cells were sorted at a concentration of $10^6$ cells/ml in PBS/2% FBS using a FACSAriaTMII (BD) cell sorter (Upenn Flow Cytometry Facility). PDGFRA+/c-Kit-fibroblasts were sorted from P1 fetal hFs and cultured as P0. For magnetic bead sorting, the Miltenyi MACS bead sorting system was used according to the manufacturer's guidelines. Data were analyzed using FlowJo software (Treestar).

Immunofluorescence and Immunochemistry

Monolayer cells were fixed with 4% paraformaldehyde and stained with primary antibodies specific for TYR, TYRP1, DCT (polyclonal; a gift from Dr. V. J. Hearing, Bethesda, Md.), Melan-A, SILV and S100 (polyclonal; Dako). After washing, cells were incubated with the appropriate Alexa Fluor® 594-labeled secondary antibodies (Invitrogen). Paraffin-embedded slides were deparaffinized, followed by antigen retrieval and staining as described above.

Immunofluorescence for DCT was performed as described above. Immunohistochemical staining for S100, melan-A and Fontana-Masson was performed on paraffin-embedded slides using standard immunoperoxidase techniques.

qRT-PCR

RNA was extracted from single cultures, using RNA mini kits (Qiagen) according to manufacturer's instructions. We performed reverse transcription reactions using SuperScript™ III First-Strand Synthesis Kit (Invitrogen). qPCR was performed using SYBR Green Supermix (Bio-Rad) and reactions were analyzed using the Bio-Rad qPCR detection system. The primers used are listed in Table 1.

TABLE 1

Primer Sequences

| Gene | Forward Sequence | Reverse Sequence | Application |
|---|---|---|---|
| MITF-M (Mus) | GCTGGAAATGCTAGAATACAG (1) | TTCCAGGCTGATGATGTCATC (2) | RT-PCR |
| Pax3 (Mus) | ATGGTTGCGTCTCTAAGATCCTG (3) | GCGTCCTTGAGCAATTTGTC (4) | RT-PCR |
| Sox10 (Mus) | TTCAGGCTCACTACAAGAGTG (5) | TCAGAGATGGCAGTGTAGAGG (6) | RT-PCR |
| Tyr (Mus) | CTTCTTCTCCTCCTGGCAGATC (7) | TGGGGGTTTTGGCTTTGTC (8) | RT-PCR |
| TYRP1 (Mus) | GCCCCAACTCTGTCTTTTCTCAAT (9) | GATCGGCGTTATACCTCCTTAGC (10) | RT-PCR |
| Dct (Mus) | GGACCGGCCCCGACTGTAATC (11) | GTAGGGCAACGCAAAGGACTCAT (12) | RT-PCR |
| Gpr143 (Mus) | ACTGCAACTGGGTCCTGCAAC (13) | TGGCAGCAAGAACACAATCCA (14) | RT-PCR |
| Silv (Mus) | ATGCGCCTAGAGAACAAAGAC (15) | TAGCAGGTTTGACGGTCAGC (16) | RT-PCR |
| MITF-M (Endo) | CGTGACCCTTTCTCCTGTAAG (17) | TTATAAAATGGAAAGGGTTAGT (18) | RT-PCR |
| PAX3 (Endo) | TCCAGCAGCAAAGCCCCAG (19) | GTGAGCAGGCCCTTCTCAGGT (20) | RT-PCR |
| SOX10 (Endo) | AATAGGAGACAAAGGAGAGTG (21) | CTTAAAATGTTGCATTTGTCT (22) | RT-PCR |
| TYR | CAGCCCAGCATCATTCTTCTC (23) | GGATTACGCCGTAAAGGTCCCTC (24) | RT-PCR |
| TYRP1 | CCTGCGTCTGGAGAAAGAC (25) | GGATCCCATCAAGTCATCCGTG (26) | RT-PCR |
| DCT | TCTGTTAGAGATACATTATTAG (27) | GACTCATTGCCAATGAGTCGCT (28) | RT-PCR |
| P | CCAGAGACTTGACTGCTGGAG (29) | TGCCCATCTGGCAATACCT (30) | RT-PCR |
| SILV | CATTCCTCACAAAAGGGAG (31) | CGTGACCCTTTCTCCTGTAAG (32) | RT-PCR |
| TYR | TCTGGGCTCTGAAGACAATCT (33) | CAGTTAATAGACTACAAAACTAAT (34) | ChIP |
| TYRP1 | AAATATAAGATCTTATCATCAG (35) | TTTTATTCTGTTATTCAACTGTT (36) | ChIP |
| TYR | TAACGTGAGATATCCCCACAATG (37) | TATCACATGTCTTGGCTGAGAC (38) | Bisulfite sequencing |
| TYRP1 | CATTTCCAATTTGGATGCTCT (39) | TAAGTGCATGTGGATTGCTG (40) | Bisulfite sequencing |

Global Gene Profiling and Array Analysis

Micro-array raw data generated from Illumina Chips were normalized, background-corrected, and summarized using the R package "lumi" (9). To reduce false positives, unexpressed probes were removed from analysis and 21,758 probes were examined in all experiments described herein. The R package "limma" (10, 11) was used to evaluate differential gene expression analysis, followed by multiple test correction by the Benjamini and Hochberg procedure (12, 13). The genes with the adjusted p values <0.05 and fold changes >4 were subjected to the two-way clustering analysis to generate the heat maps. GSEA analysis was performed as described previously (14).

Bisulfite Genomic Sequencing

Bisulfite treatment was performed using the CpGenome modification Kit (Millipore), according to the manufacturer's recommendations. The PCR primers used are listed in Table 1. Amplified products were cloned into pCR2.1-TOPO (Invitrogen). Ten randomly selected clones were sequenced with the M13 forward and M13 reverse primers for each gene. Sequencing was performed at the University of Pennsylvania sequencing facility. CpG methylation of the sequence was analyzed by BiQ Analyzer software.

Chromatin Immunoprecipitation $10^7$ hFFs, hiMels or human melanocytes were fixed with 1% formaldehyde at room temperature for 10 min and then lysed in 1 ml lysis buffer (50 mM Tris-HCl, pH 8.0, 10 mM EDTA, 1% SDS, and protease inhibitors) on ice for 20 min. The lysate was split into three tubes and sonicated. After 10 min centrifugation, the supernatant was pre-cleared by incubating at 4° C. for 4 h with agarose beads pre-blocked with BSA (1 mg BSA for 10 ml beads) in IP buffer (50 mM Tris-HCl, pH 8.0, 150 mM NaCl, 2 mM EDTA, 1% NP-40, 0.5% sodium deoxycholate, 0.1% SDS, protease inhibitors). A total of 100 µl of pre-cleared chromatin per reaction diluted in 1 ml IP buffer in the presence of 20 µg antibody was used for each immunoprecipitation reaction, according to the manufacturer's protocol. The antibodies used for this study were: anti-acH3 (Millipore), anti-dimethyl K4 of H3 (H3K4me2, Millipore), and normal rabbit IgG (Sigma). The precipitate was purified and analyzed by qPCR. PCR primers were listed in Table 2.

Sphere Formation Assay

Sphere formation assay was performed as described previously (15). Briefly, dissociated cells were plated in serum-free media in low-cell-density cultures with exogenous growth factors used at final concentrations of 10 ng/ml bFGF and 100 ng/ml SCF. Sphere colonies were generated and counted under the microscopy.

Human 3D Skin Reconstructions

Human 3D skin reconstructions were generated as described previously (16). Briefly, inserts of tissue culture trays (Organogenesis, Canton, Mass.) were coated with 1 ml bovine collagen I (Organogenesis) and layered with 3 ml collagen I containing $7.5 \times 10^4$ fibroblasts. After 4 to 7 days at 37° C., hiMels were mixed with keratinocytes and seeded on top of the dermal reconstructions at a ratio of 1:5 (hiMels to keratinocytes). After 4 days, human keratinocytes were added and the cells were cultured in skin reconstruct media: keratinocyte serum-free medium (Invitrogen) with 60 µg/ml bovine pituitary extract, 2% dialyzed fetal bovine serum (FBS, Invitrogen), 4.5 ng/ml bFGF (Invitrogen), 100 nM ET-3 (sigma), and 10 ng/ml SCF (R&D system). Cultures were submerged in media containing 1 ng/ml epidermal growth factor (EGF) (Invitrogen) for 2 days, 0.2 ng/ml EGF for another 2 days, then maintained at the air-liquid interface and incubated in high-calcium (2.4 mM) media. Two weeks later, skin reconstructions were harvested, fixed in 10% neutral buffered formalin for 3 hours, and processed by routine histological methods. For a-MSH treatment assay, 50 nM a-MSH was added in the culture to induce melanin production in the reconstructed skin.

Hair Patch Assays with Melanocytes

Patch assays were performed as previously described (17, 18). Briefly, truncal skin from one day postnatal BALB/c mice, a mouse strain with non-pigmented white hair coat, was removed and rinsed in free PBS. The skin was laid flat in PBS containing Dispase (2.5 mg/ml, Invitrogen) at 4° C. overnight. Epidermis and dermis were separated and inductive dermal cells and epidermal cells were isolated as previously described (19, 20). Trichogenic cells were assayed in male nude (nu/nu) mice (Charles River) at 7-9 weeks. For each intracutaneous injection, $1 \times 10^6$ BALB/c neonatal dermal cells and 10,000 epidermal aggregates were used. In order to test the ability of hiMels to participate in the formation of hair follicles and produce pigmented shafts in the reconstitution assay, $0.5 \times 10^6$ hiMels were added to the neonatal BALB/c dermal and epidermal cell mixture for each injection. As positive controls, $0.5 \times 10^6$ cultured human melanocytes were added in separate injections with the mouse cells. The cell mixtures were resuspended in 50-70 µl of DMEM-F12 medium (Invitrogen) and injected (25-gauge needle) into the hypodermis of the mouse skin, forming a bleb. The injection site was marked by a black tattoo puncture (242 Permanent Black Pigment, Aims, Hornell, N.Y.). The skin was harvested at two weeks after injection and the newly formed hair follicles were examined under a dissection microscope. Two independent experiments with different batches of hiMels were performed, with 2 duplicate sets each time.

In Situ Hybridization

Briefly, paraffin slides were dehydrated, antigen retrieved, and hybridized with Alu DNA probe (BioGenex PR-1001-01, ready-to-use): heat slide to 85° C. 10 min, and then 37° C. overnight. The slides were then incubated with antibody specific for fluorescein, biotin-labeled (BioGenex AS2505-16, ready to use), and finally incubated with secondary antibody labeled with Streptavidin-Alexa Fluo488. DAPI was used to label nuclear DNA.

Statistical Analysis

Student's t-test or ANOVA was used to analyze gene expression and flow cytometric data. qPCR data were analyzed after being normalized for β-actin loading control. Statistical significance was determined if two-sided $p<0.05$.

The following example is provided to illustrate certain embodiments of the invention. It is not intended to limit the invention in any way.

Example I

Previous studies have demonstrated a critical role for microphthalmia-associated transcription factor (MITF) in melanocyte linage determination from neural crest cells and forced expression of MITF in NIH3T3 fibroblasts converted them into melanocyte-like cells (21). However, such induced cells expressed only some of the melanocyte specific markers and lacked functional characteristics of melanocytes (21). Reasoning that multiple transcription factors would probably be required to reprogram fibroblasts into functional melanocytes, we selected 10 candidate transcription factors that are related to neural crest lineage determination and melanocyte differentiation (Table 2) (22-29).

TABLE 2

Candidate Transcription Factors

| Gene name | Genebank number |
| --- | --- |
| hSOX10 | NM_006941 |
| hMITF | NM_198159 |
| hPAX3 | NM_181459 |
| mSOX10 | NM_011437 |
| mMITF | NM_001113198 |
| mPAX3 | NM_008781 |
| mDLX5 | NM_010056 |
| mFOXD3 | NM_010425 |
| mLEF1 | NM_010703 |
| mMSX1 | NM_010835 |
| mPAX6 | NM_001244200 |
| mSOX2 | NM_011443 |
| mSOX9 | NM_011448 |

To efficiently monitor melanocyte differentiation by flow cytometric analysis, we developed a transcription factor screening assay using tail fibroblasts (TTFs) from Tyrosinase-CreER; Gt(ROSA)26Sor$^{tm4(ACTB-tdTomato-EGFP)Luo}$/J reporter mice (30). Tyrosinase (TYR)-driven CreER-expression in melanocytes converts these mouse cells from expressing red fluorescent protein (RFP) to green fluorescent protein (GFP) upon treatment with 4-hydroxytamoxifen (4-HT). This makes it possible to monitor the emergence of TYR-positive (TYR+) melanocytes by detecting GFP expression (FIG. 1a). Retroviruses carrying the 10 candidate mouse transcription factors were prepared and a mixture of all the factors was used to infect the TTFs. Expression of transgenes was confirmed by qRT-PCR (FIG. 2) and virus packaged with vector only was used as a negative control. Twelve days after infection with all factors, GFP-positive (GFP+) cells were observed in the presence of 4-HT (FIG. 1b), indicating activation of the TYR promoter in cells. Significantly fewer GFP+ cells were detected in the control, vector only cells (FIG. 1b).

Figure 3A:
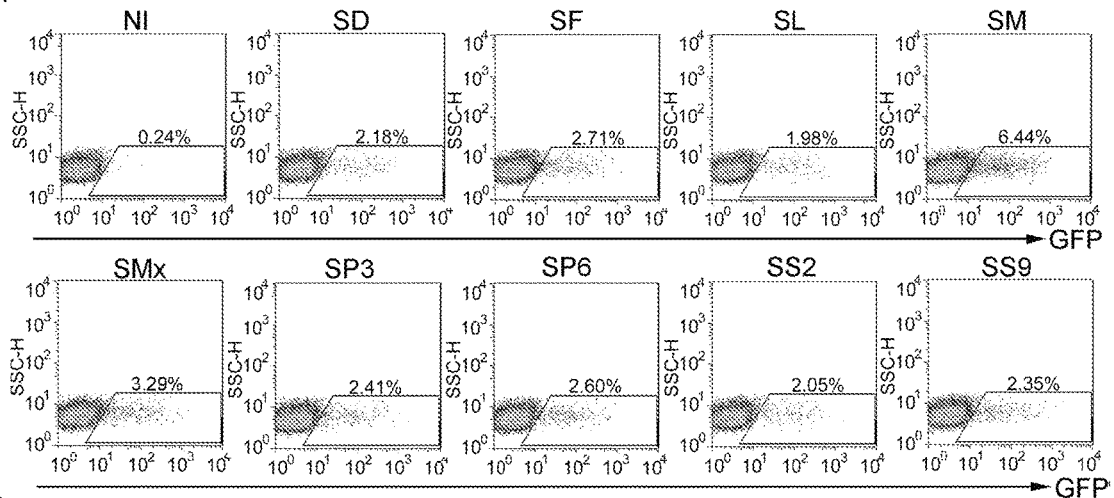
FIGS. 3A-3C. Flow cytometric analysis of the percentage of GFP positive (GFP+) cells after infection. TTFs derived from Tyrosinase-CreER/Gt(ROSA)26-Sor$^{tm4(ACTB-tdTomato-EGFP)Luo}$/J mice were infected with viruses containing different combinations of candidate factors. Flow cytometric analysis was performed 5 days after infection. Flow cytometric analysis of the percentage of GFP+ cells when the TTFs were infected with viruses carrying 2 different candidate factors (FIG. 3A); 3 different candidate factors (FIG. 3B) or 4 different candidate factors (FIG. 3C). NI: vector only; S: SOX10; D: DLX5; F: FOXD3; L: LEF1; M: MITF; Mx: MSX1; P3:PAX3; P6: PAX6; S2:SOX2; S9: SOX9.
Figure 3B:
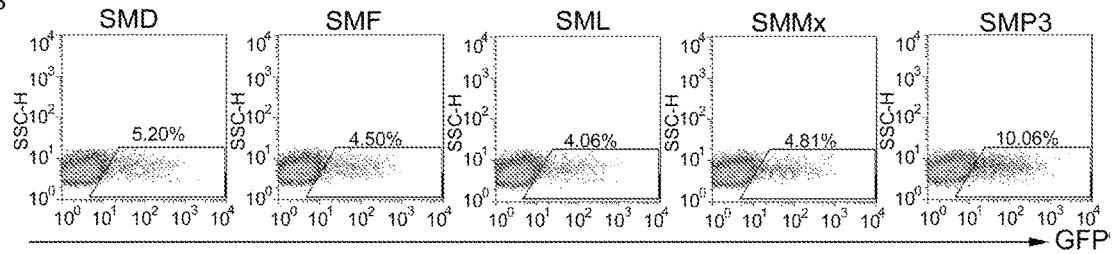
Figure 3B:
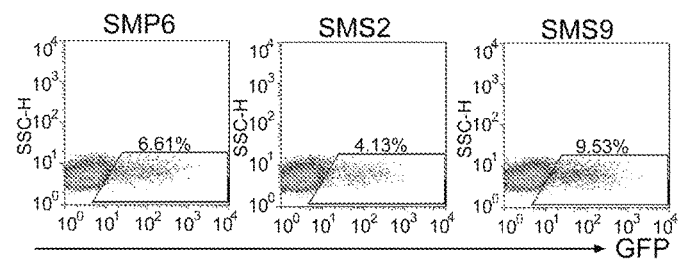
Figure 3C:
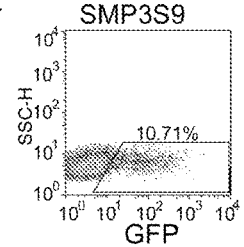
Figure 4A:
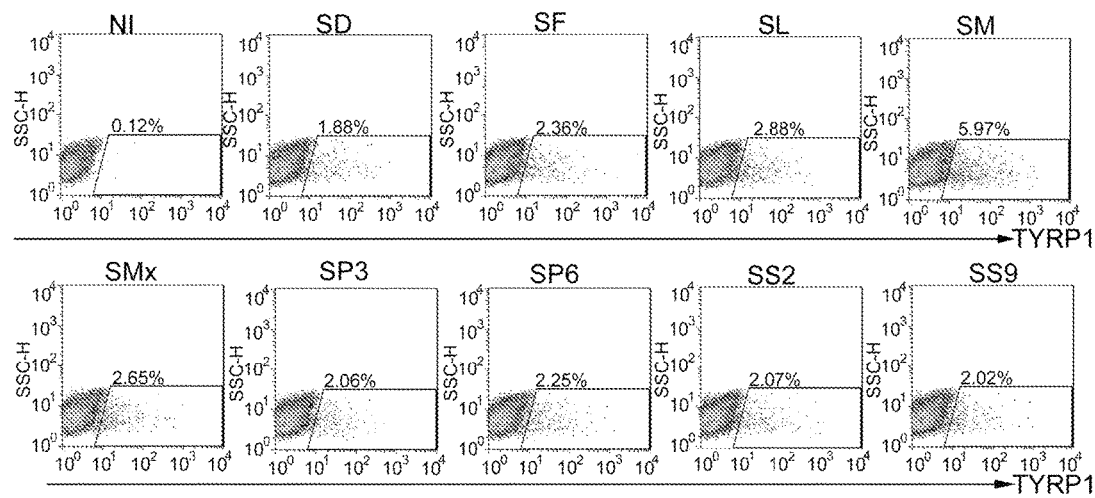
FIGS. 4A-4C. Flow cytometric analysis of the percentage of TYRP1 positive (TYRP1+) cells after infection. TTFs derived from Tyrosinase-CreER/Gt(ROSA)26-Sor$^{tm4(ACTB-tdTomato-EGFP)Luo}$/J mice were infected with viruses carrying different combinations of the candidate factors. Flow cytometric analysis was performed 5 days after infection. Flow cytometric analysis of the percentage of TYRP1+ cells when TTFs were infected with virus containing 2 different candidate factors (FIG. 4A); 3 different candidate factors (FIG. 4B) or 4 different candidate factors (FIG. 4C).
Figure 4B:
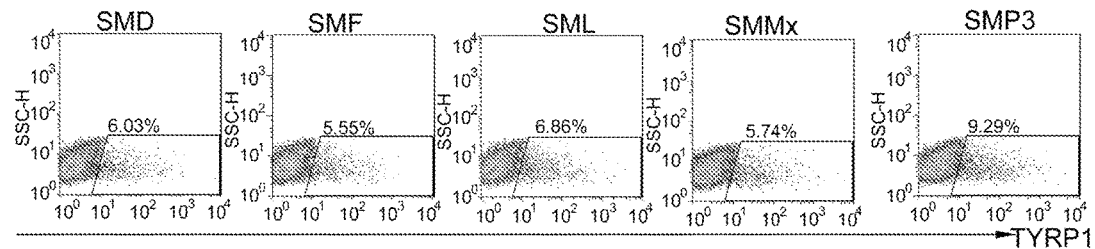
Figure 4C:
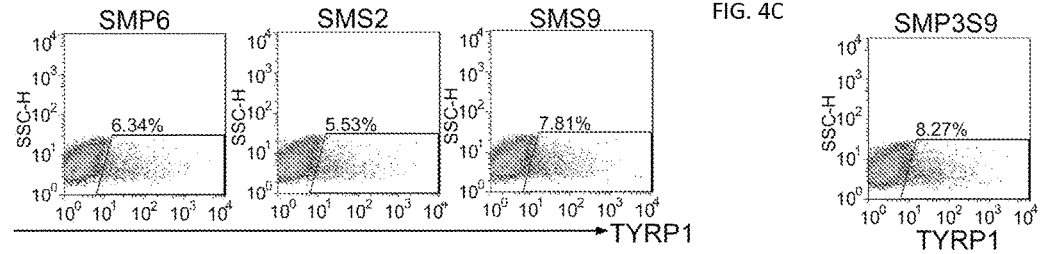
Figure 5:
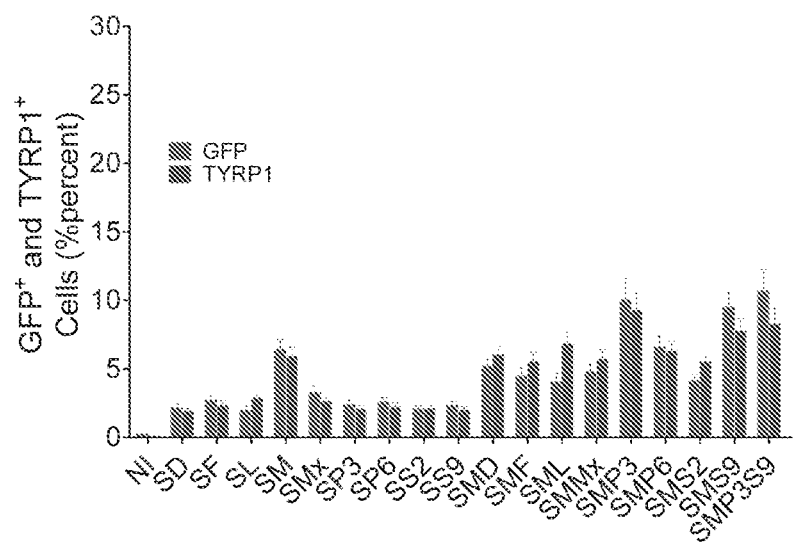
FIG. 5. Quantification of GFP+ and TYRP1+ cells by flow cytometric analysis as shown in FIGS. 4 and 5. Data shown are mean±SD from three independent experiments.

We next sought to determine the minimal set of genes required for melanocyte induction from fibroblasts. Given the known dominant role of SOX10 during neural crest lineage differentiation, SOX10 was introduced into TTFs combined with every other single factor. The greatest number of GFP+ cells was produced when SOX10 was combined with MITF (FIG. 3a). However, the SOX10/MITF combination elicited modest reprogramming efficiencies with GFP+ cells comprising 6.44% of all cells. Therefore, we added a third transcription factor (from the 8 remaining) and analyzed the percentage of GFP+ cells using each combination. SOX10/MITF/PAX3 and SOX10/MITF/SOX9 combinations increased the generation of GFP+ cells, compared to other combinations (FIG. 3b). The addition of SOX9 to the SOX10/MITF/PAX3 combination failed to further increase the percentage of GFP+ cells, compared to the SOX10/MITF/PAX3 or SOX10/MITF/SOX9 combinations (FIG. 3c). Furthermore, the addition of a fourth factor to the SOX10/MITF/PAX3 or SOX10/MITF/SOX9 combinations failed to further increase the percentage of GFP+ cells (data not shown). To confirm melanocytic reprogramming, we examined the percentage of TYRP1-positive (TYRP1+) cells using flow cytometric analysis after reprogramming with different combinations of transcription factors. The results demonstrated that the SOX10/MITF/PAX3 combination induced the highest percentage of TYRP1+ cells (FIG. 4). Statistical analysis showed that the SOX10/MITF/PAX3 combination activated higher GFP and TYRP1 expression, compared to other combinations (FIG. 1c and FIG. 5). Therefore, melanocytes induced by SOX10/MITF/PAX3 (SMP3) were characterized in additional studies.

Figure 6A:
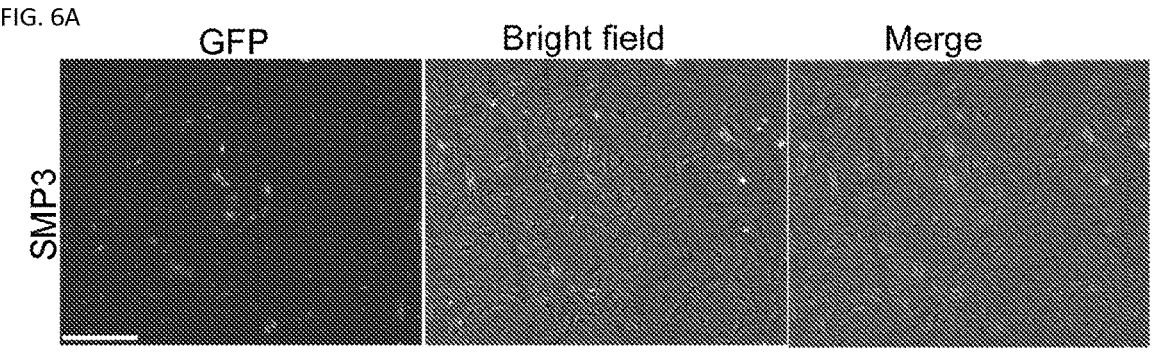
FIGS. 6A-6B. Morphology of GFP+ cells after direct reprogramming by SMP3. Representative images of TTFs derived from Tyrosinase-CreER/Gt(ROSA)26-Sor$^{tm4(ACTB-tdTomato-EGFP)Luo}$/J mice infected with SMP3 for 14 days. GFP+ cells were detected among the SMP3 infected cells and photographed at Day 14 (FIG. 6A). GFP+ cells were enriched after FAGS sorting and these cells showed typical melanocytic morphology (FIG. 6B). Scale bar, 50 μm.
Figure 6B:
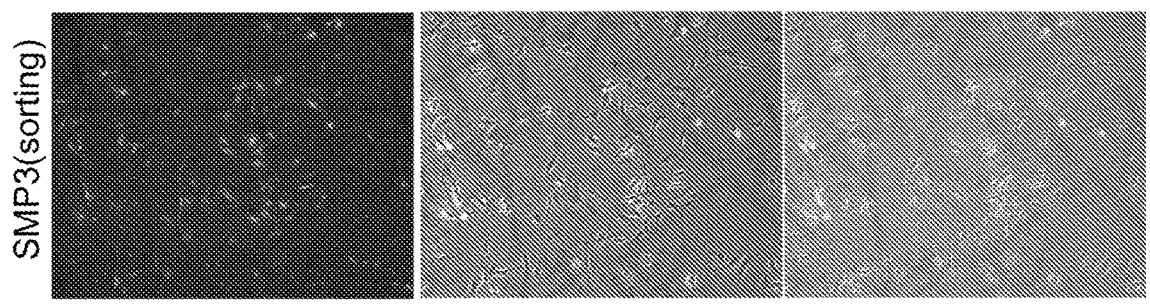
Figure 7:
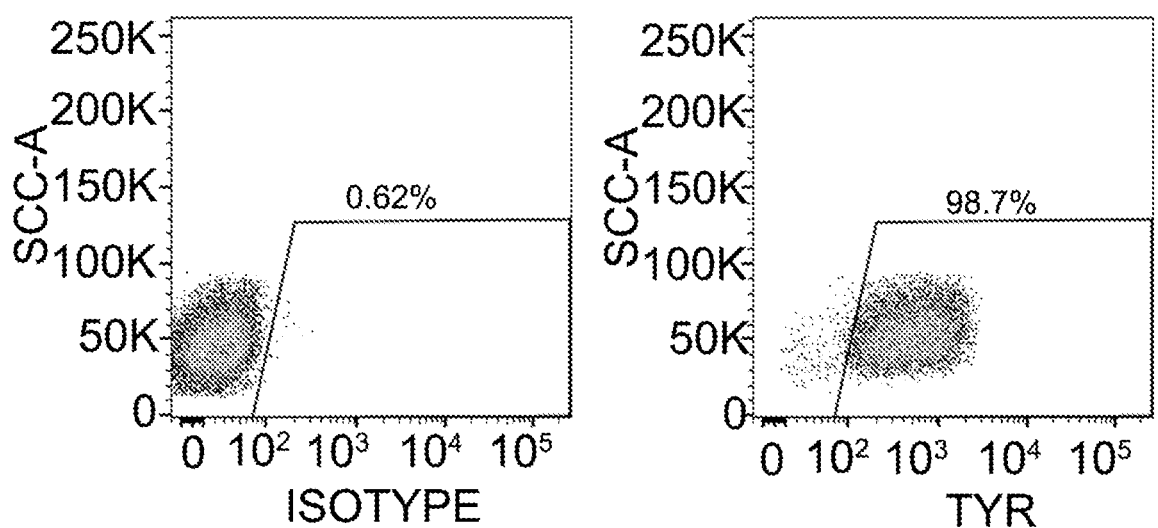
FIG. 7. Flow cytometry analysis of the percentage of TYR+ cells among GFP+ cells. TTFs derived from Tyrosinase-CreER/Gt(ROSA)26Sor$^{tm4(ACTB-tdTomato-EGFP)Luo}$/J mice were infected with SMP3 for 14 days. TYR+ cells were gated from the GFP+ cells. Representative results are from 3 independent experiments.
Figure 8A:
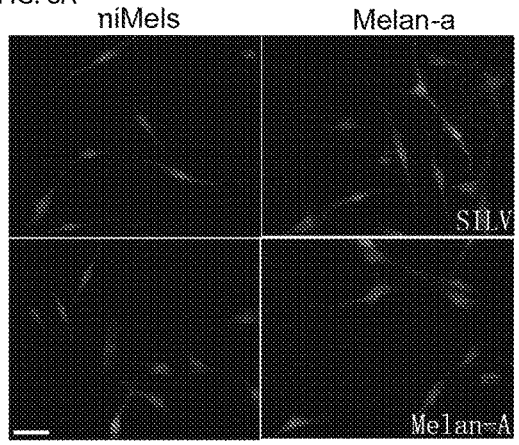
FIGS. 8A-8C. Characterization of directly reprogrammed mouse iMels.
Figure 8B:
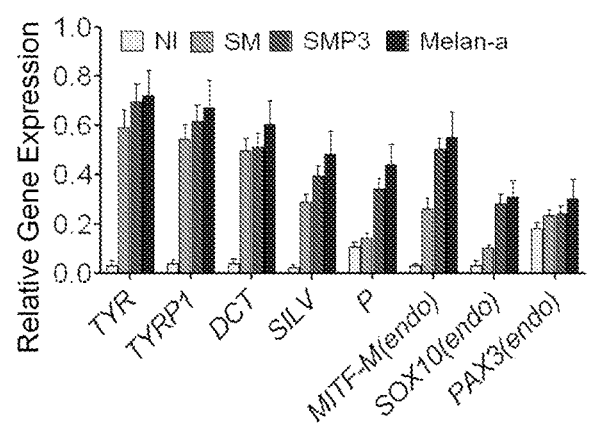
Figure 8C:
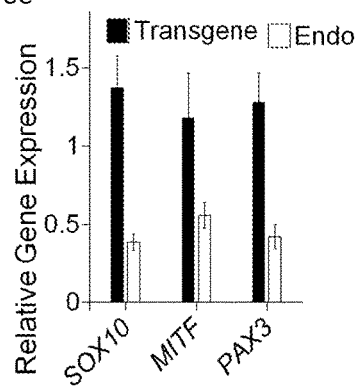

We monitored the GFP+ cell population daily under a fluorescent microscope after TTFs derived from Tyrosinase (TYR)-CreER/Gt(ROSA)26Sor$^{tm4(ACTB-tdTomato-EGFP)Luo}$/J mice were infected with virus carrying the SMP3 combination. GFP+ cells with melanocytic morphology emerged 14 days after induction (FIG. 1d, and FIGS. 6a and 6b). GFP+ cells were sorted out using FACS and reseeded for further characterization. These cells expressed the protein components of pigment production and delivery machineries including TYR, DCT, Melan-A and SILV (FIGS. 1e and 1f, and FIGS. 7 and 8a). We also observed that S100, a calcium binding protein, is highly expressed in the induced melanocytes (FIG. 1g). Transcriptional analysis by reverse transcription polymerase chain reaction (RT-PCR) revealed the expression of multiple melanocyte-specific genes, including TYR, TYRP1, DCT, SILV, P as well as endogenous MITF, SOX10 and PAX3 (FIG. 8b). Meanwhile, transgenic SOX10, MITF and PAX3 were still expressed in the GFP+ cells (FIG. 8c). Electron microscopy (EM) showed that GFP+ iMels produced melanosomes at different developmental stages (FIG. 1h), including mature melanin-containing (types III and IV) melanosomes.

Figure 9A:
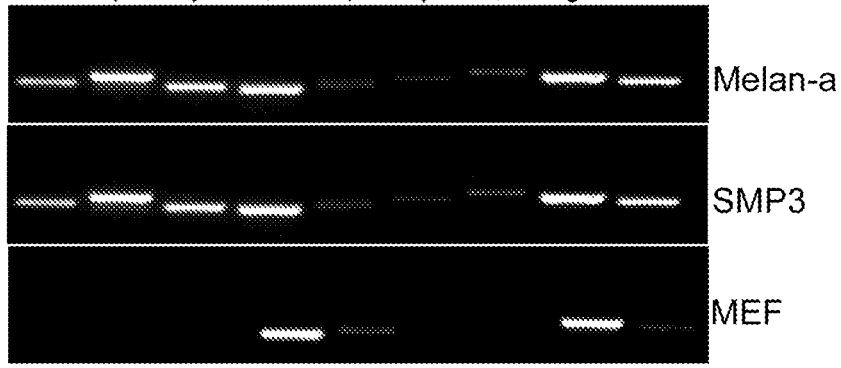
FIGS. 9A-9B. Melanocytic marker expression and DOPA activity in mouse SMP3 induced MEFs.
Figure 9B:
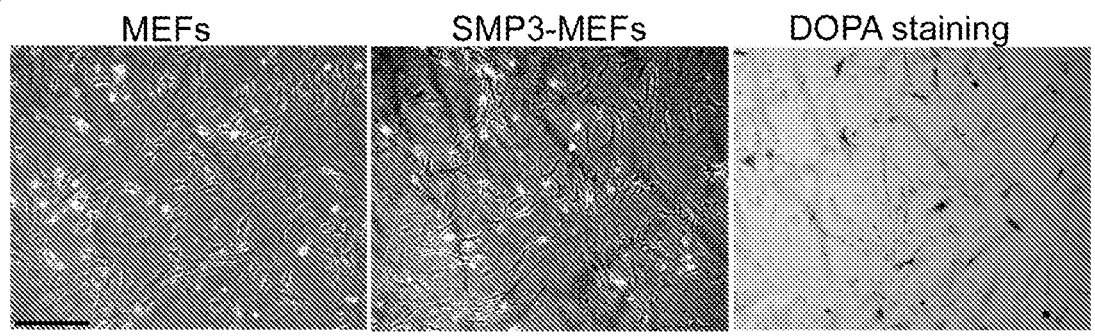
Figure 10A:
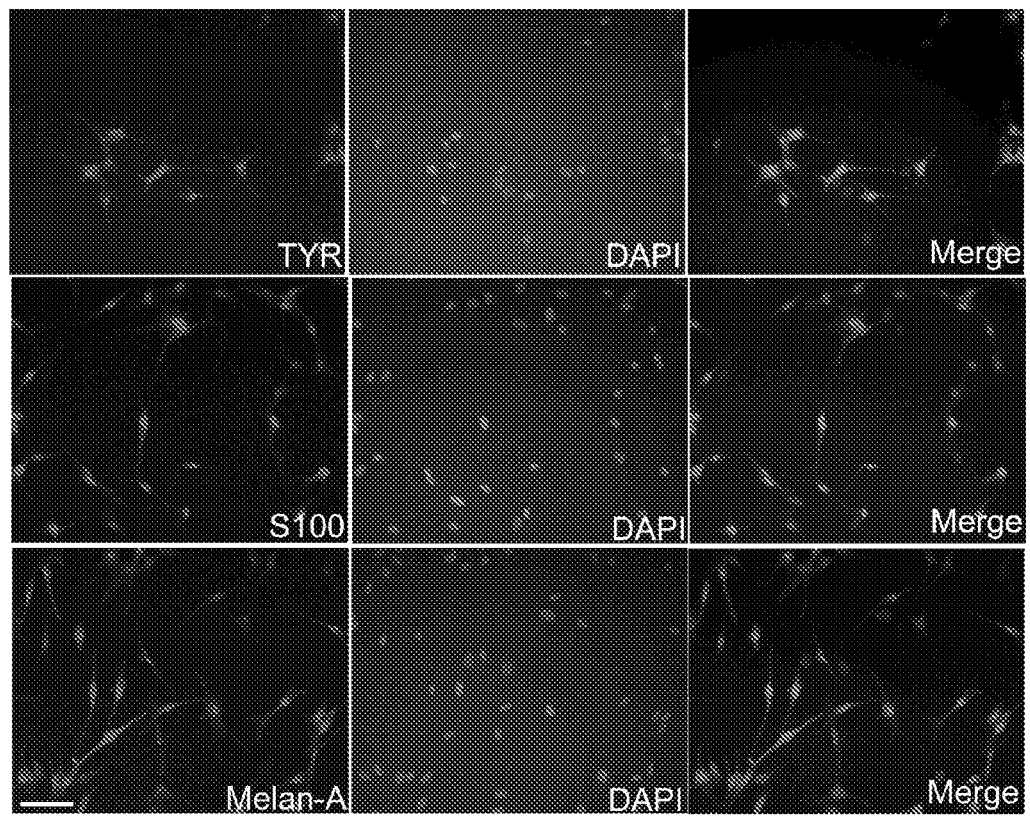
FIGS. 10A-10B. Characterization of directly reprogrammed mouse iMels from MEFs. MEFs were reprogrammed into iMels by SMP3.
Figure 10B:
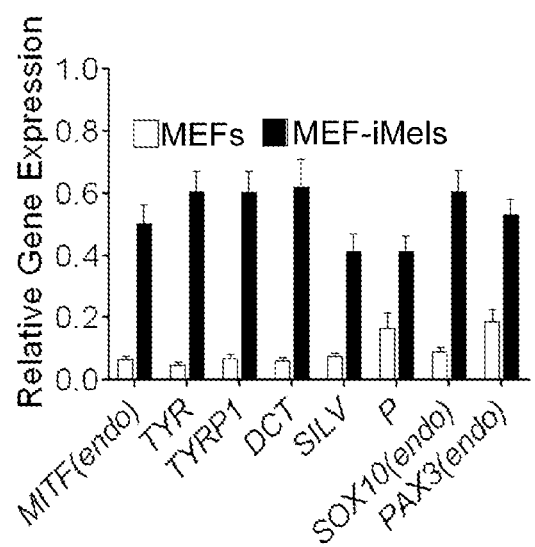
Figure 11A:
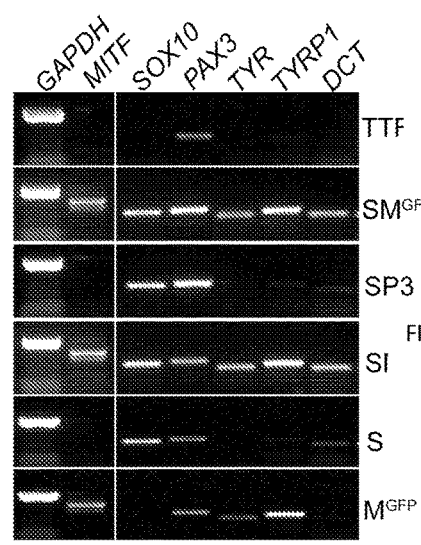
Figure 11A:
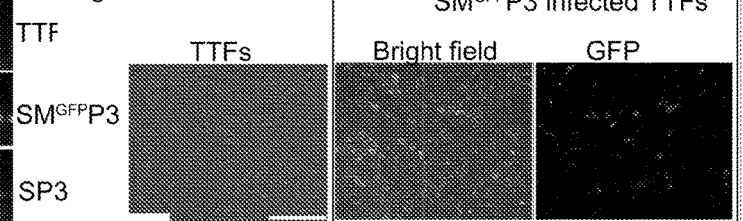
Figure 11A:
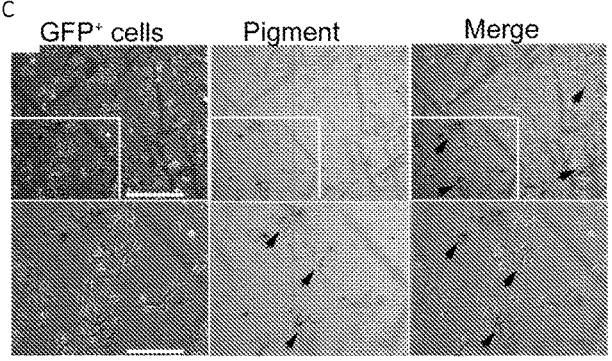
Figure 11D:
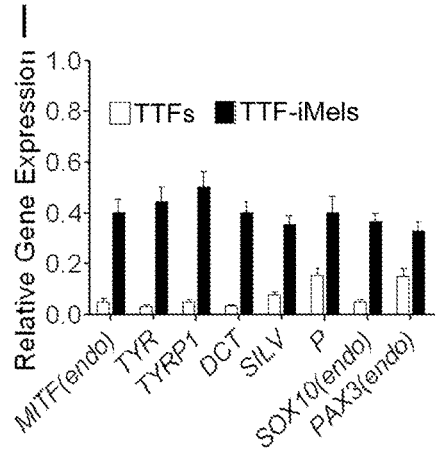

We then tested the SMP3 combination in mouse embryonic fibroblasts (MEFs) and TTFs derived from adult C57BL/6 mice. We found that melanocyte-specific markers, including TYR, TYRP1 and DCT were expressed as early as 5 days after MEF cells were infected with the SMP3 combination (FIG. 9a). Since melanocytes are more resistant to G418 than fibroblasts (31), we cultured the SMP3-infeced MEFs on layers of XB2 keratinocyte feeder cells for 14 days with G418. G418-resistant cells with typical melanocyte morphology showed strong Dopa activity (FIG. 9b). The majority of the G418-resistant cells expressed TYR, Melan-A and S100 (FIG. 10a) and displayed melanocyte-specific gene expression patterns (FIG. 10b). Similar results were obtained when adult TTFs were infected with the SOX10, MITF-GFP and PAX3 (SMGFPP3) combination and these adult TTFs expressed melanocytic markers after infection with SMGFPP3 (FIG. 11a). GFP+ cells (FIG. 11b) were sorted out using FACS and cultured in melanocyte inducing medium. As expected, the reprogrammed GFP+ cells showing typical melanocyte morphologies (FIG. 11c) displayed higher expression levels of melanocytic markers, compared to adult TTFs infected with vector only (FIG. 11d).

Figure 12A:
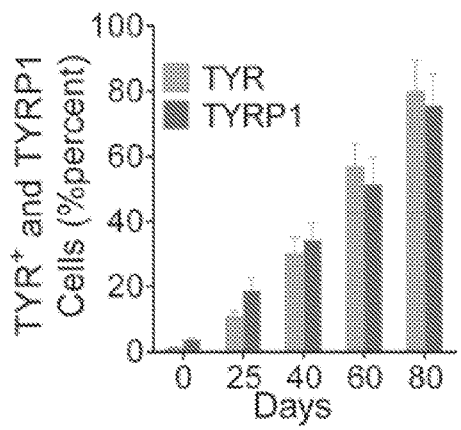
FIGS. 12A-12I. Direct reprogramming of human fibroblasts to melanocytes FIG. 12A. Percentage of TYR+ and TYRP1+ cells after reprogramming with SMGFPP3 at indicated time points. Human fetal fibroblasts (fetal hFs) were infected with SMGFPP3, sorted and selected in media containing G418. Cells were analyzed by flow cytometric analysis at Day 0, 25, 40 and 80. Representative data are from three independent experiments.
Figure 12B:
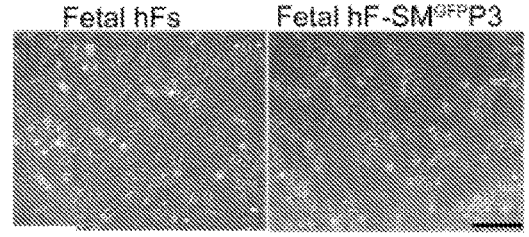
Figure 12G:
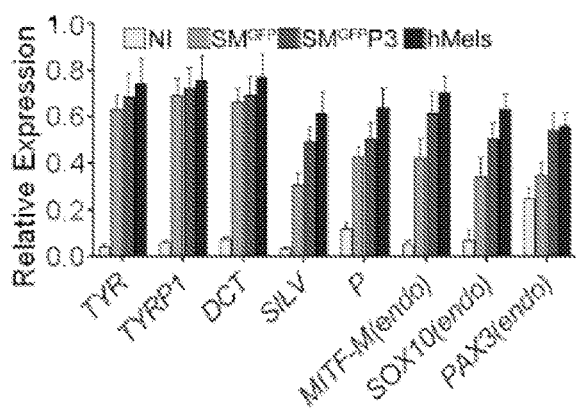
Figure 12C:
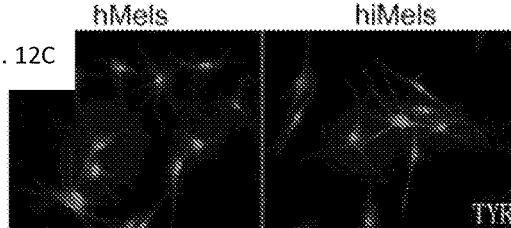
Figure 12D:
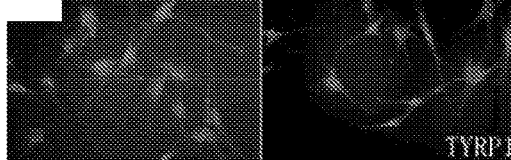
Figure 12E:
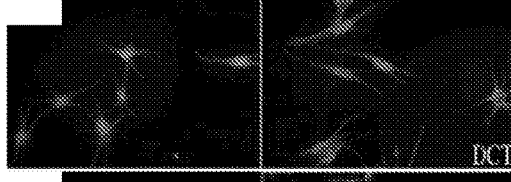
Figure 12F:
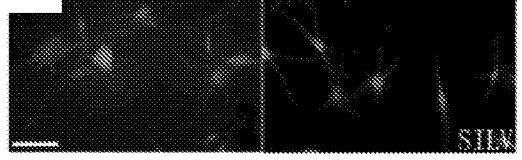
Figure 12H:
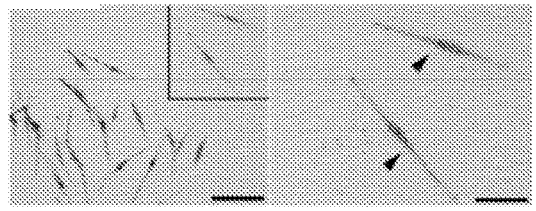
Figure 12I:
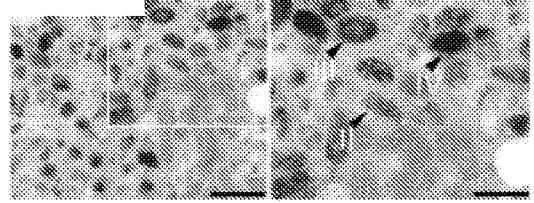
Figure 13A:
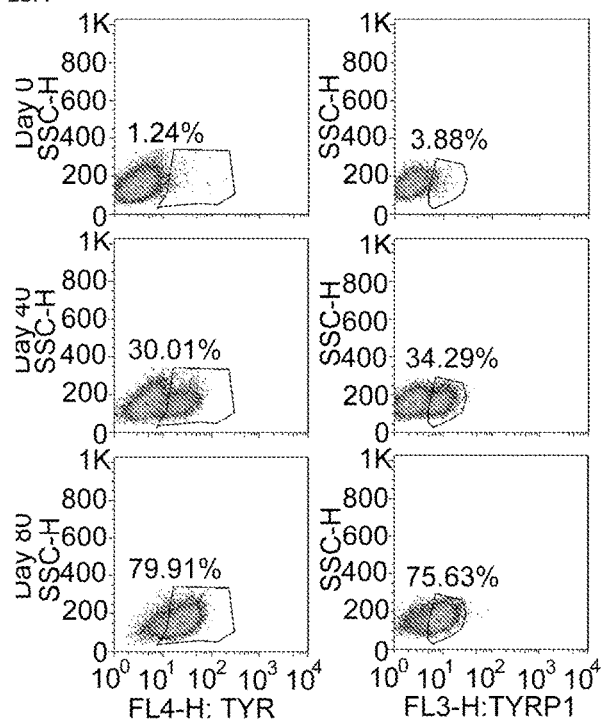
FIGS. 13A-13D. Characterization of directly reprogrammed human iMels from fetal fibroblasts. Passage 2 human fetal fibroblasts (fetal hFs) were infected with viruses carrying SMGFPP3.
Figure 13B:
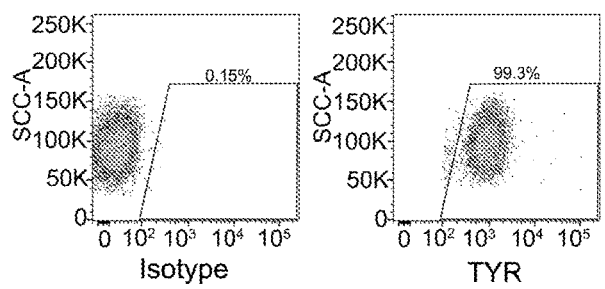
Figure 13C:
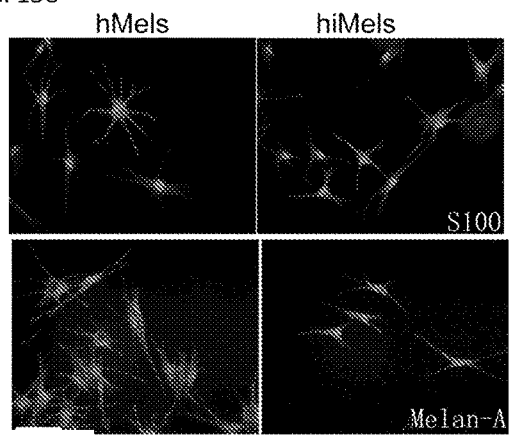
Figure 13D:
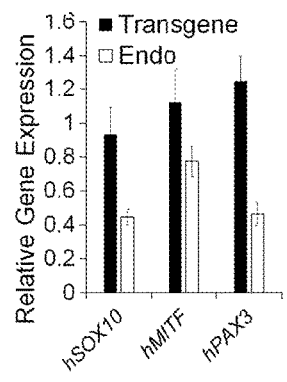
Figure 14A:
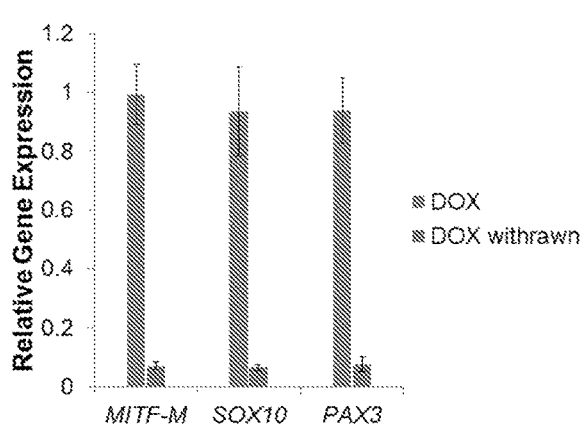
FIGS. 14A-14C. Generation of hiMels using inducible system. Human MITF-M, SOX10 and PAX3 were subcloned into inducible viral vectors. Fetal hFs were infected with viruses carrying these transgenes.
Figure 14C:
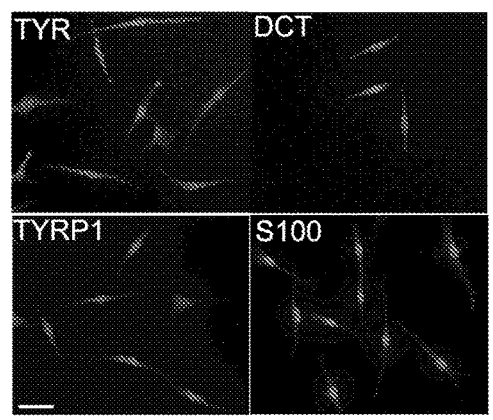
Figure 14B:
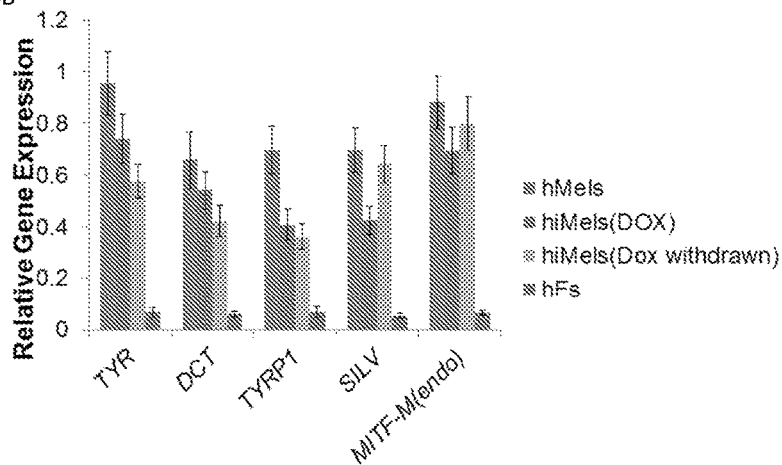

To test whether human fibroblasts can be directly reprogrammed into melanocytes, we infected passaged primary human fetal dermal fibroblasts (fetal hFs) with the human SMGFPP3 combination. SMGFPP3-infected cells were cultured under G418 selection until the cell population with typical melanocyte morphology overwhelmed other cell populations. During this process, we analyzed the percentage of TYR+ and TYRP1+ cells in the culture using flow cytometric analysis. About 40% of cells with typical melanocyte morphology were observed by Day 40 (FIGS. 12a and 12b, FIG. 13a), and the majority of the cells showed typical melanocyte immuno-phenotypes by Day 80 (FIG. 12a and FIG. 13a). We continued to culture these melanocytic cells and found that 99.3% of the enriched cells were TYR+ cells (FIG. 13b) at Day 100. hiMels expressed TYR, TYRP1, DCT and SILV (FIG. 12c-12f), as well as S100 and Melan-A (FIG. 13c). qRT-PCR analysis further confirmed that the melanocyte-specific gene network was activated (FIG. 12g). In addition, endogenous expression of PAX3, SOX10 and MITF was also induced (FIG. 12g). However, we found that transgenic PAX3, SOX10 and MITF were still expressed in hiMels (FIG. 13d). Concerned that the melanocyte phenotype and function were dependent on continued transgene expression, we introduced the viruses that express doxycycline inducible PAX3, SOX10 and MITF into fetal hFs. Transgenic expression of PAX3, SOX10 and MITF was induced for 2 weeks and then silenced by withdrawing doxycycline from the culture medium (FIG. 14a). The silenced cells were cultured for another 80 days and analyzed by qRT-PCR and immunostaining assays. The melanocytic markers continued to be expressed without exogenous PAX3, SOX10 and MITF expression (FIGS. 14b and 14c). These data indicate that the induced melanocytic phenotype is stable and independent of transgene expression. The hiMels were capable of producing melanin pigment, as revealed by Fontana-Mason staining (FIG. 12h). To further confirm the melanocyte identity, we found that hiMels contained authentic melanosomes from early stage (type II) to mature melanin-containing (types III and IV) melanosomes (FIG. 12i).

Global expression analysis showed that hiMels clustered with human adult melanocytes rather than with the parental fibroblasts, as illustrated by unsupervised hierarchical clustering (FIG. 15a). Of note, many representative genes encoding rate limiting enzymes for pigmented melanin production (such as TYR, TYRP1 and DCT) were upregulated in hiMels (FIG. 15b). In addition, Melan-A was highly expressed in hiMels (FIG. 15b). Moreover, we analyzed the MSigDB gene set collection for its enrichment in both hiMels and hMels. As shown in FIG. 15c, hiMels derived from human fibroblast gained the characteristic of melanocytes (KEGG_LYSOSOME gene set and DACOSTA_UV_RESPONSE_VIA_ERCC3 pathways) and lost the expression of fibroblast specific gene network (MILI_PSEUDOPODIA_HAPTOTAXIS_DN and MILI_PSEUDOPODIA_CHEMOTAXIS_DN pathways) (32).

We next analyzed the DNA methylation status of TYR and TYRP1 promoters, as indicators of gene activation. As expected, TYR and TYRP1 promoters were highly demethylated in hiMels (percentage of demethylation: TYR, 69.64%; TYRP1, 60.94%) and human melanocytes (percentage of demethylation: TYR, 85.71%; TYRP1, 87.5%), whereas these same regions were highly methylated in the parental fibroblasts (percentage of demethylation: TYR, 35.67%; TYRP1, 34.38%) (FIGS. 15d and 15e). We then performed chromatin immunoprecipitation (ChIP) assays to analyze histone modifications in TYR and TYRP1 promoter regions. We found that hiMels and hMels showed higher levels of H3K4me2 methylation and acH3 acetylation, compared to the parental fibroblasts (FIGS. 15f and 15g).

Figure 16A:
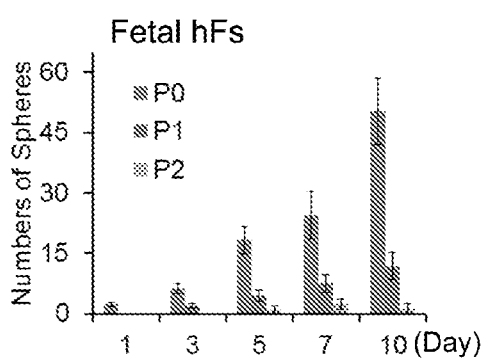
FIGS. 16A-16B. Sphere formation capacity of human fetal primary and PDGFRA+I c-Kir fibroblasts.
Figure 17A:
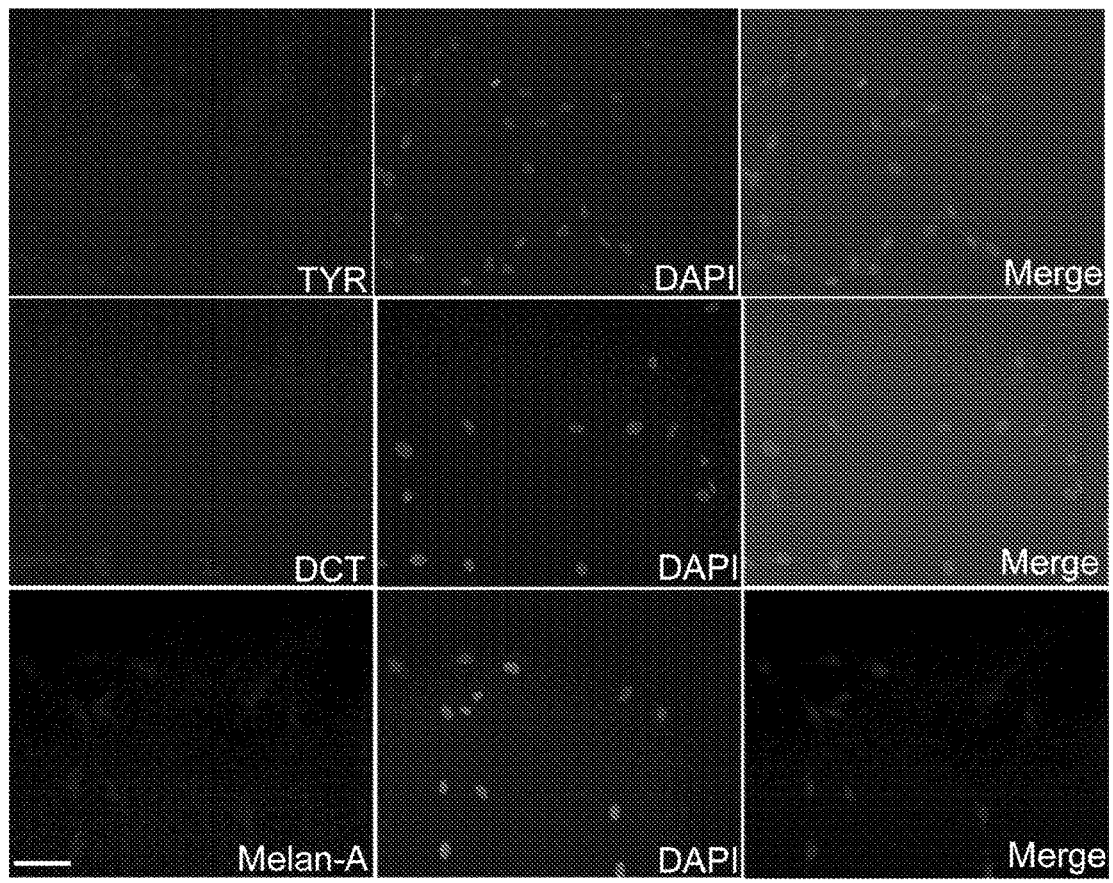
FIGS. 17A-17B. Melanocytic marker expression in human fetal fibroblasts. P2 human fetal fibroblasts (fetal hFs) were cultured in the induction medium for 40 days.
Figure 17B:
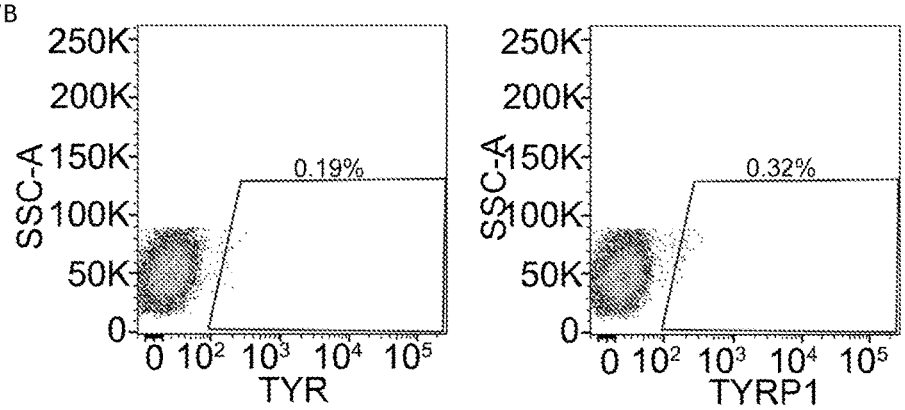

Next, we performed sphere formation assays to test the presence of adult stem cells in primary fetal fibroblasts in the current melanocyte culture condition. We found that Passage 0 (P0) primary fetal dermal fibroblasts can form some spheres; however these sphere forming cells decreased dramatically with passaging and by Passage 2 (P2) fetal fibroblasts which were used in the melanocyte induction experiments formed few spheres (FIG. 16a). To further exclude the possibility that fetal fibroblast cultures were contaminated by melanocytes or melanocyte stem cells, we cultured P2 fetal fibroblasts in the induction medium for 40 days. After this incubation period, we did not detect any cells that expressed TYR, TYRP1, DCT or Melan-A (FIG. 17a). Similarly, flow cytometric analysis showed few TYR+ or TYRP1+ cell populations in the culture (FIG. 17b).

Figure 16B:
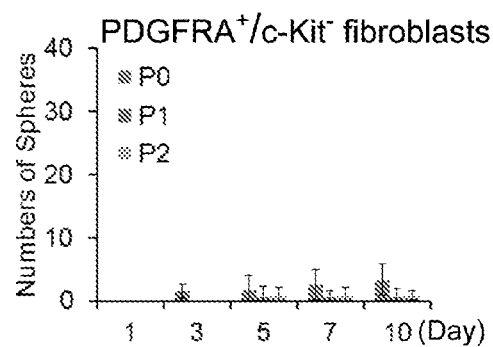
Figure 18A:
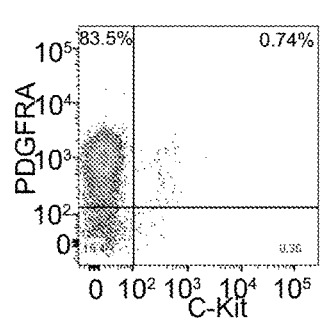
FIGS. 18A-18C. Characterization of hiMels induced from human fetal purified fibroblasts. Human fetal PDGFRA+/c-Kit fibroblasts were reprogrammed using SMGFPP3.
Figure 18B:
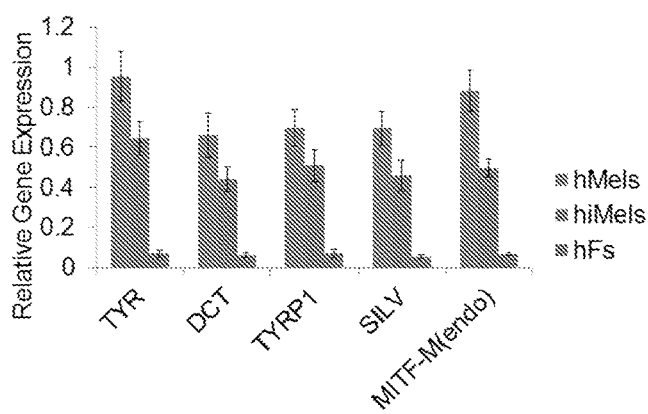
Figure 18C:
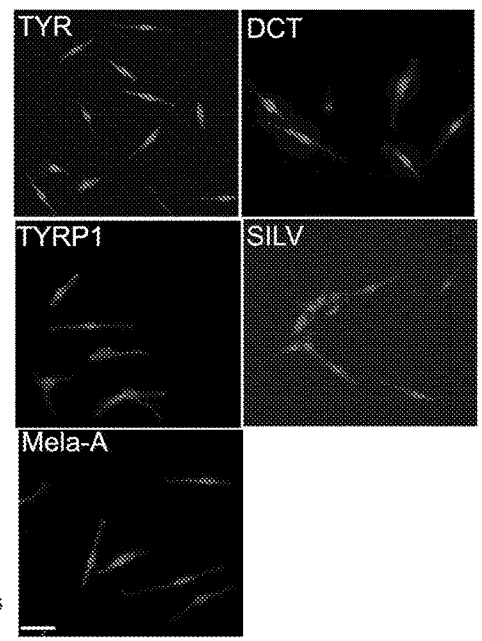

To further clarify the purity and identify of the starting fibroblast population, we used a fibroblast marker, PDGFRA (33), to purify fibroblasts and a melanocyte marker, c-Kit, to gate out melanocytes using the MACS MicroBead technology (FIG. 18a). Firstly, we found that the PDGFRA+/c-KIT- fibroblasts formed few spheres (FIG. 16b). The P2 PDGFRA+/c-KIT-purified fibroblasts were then reprogrammed by the human SMGFPP factors group. Expression of melanocytic markers was confirmed by qRT-PCR and immunostaining (FIGS. 18b and 18c). These results further indicate that iMels do not arise from culture contaminants but are directly reprogrammed from human fibroblasts.

Figure 19:
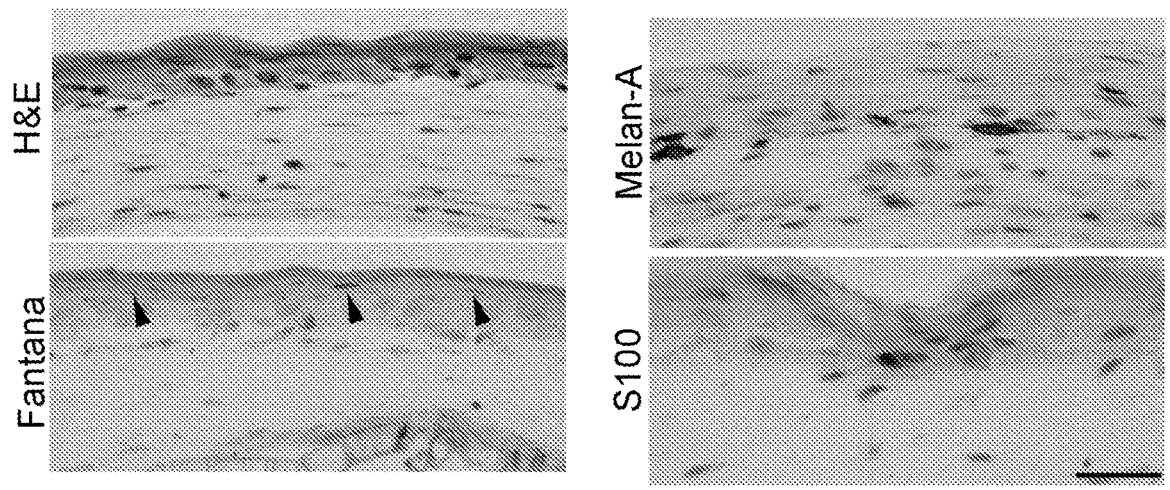
FIG. 19. hiMels derived from human fetal fibroblast in 30 skin equivalents. 30 skin equivalents were constructed using foreskin keratinocytes and hiMels. Fontana-Mason staining of 30 skin equivalents showed melanin pigment in keratinocytes, indicating transfer of pigment from melanocytes to keratinocytes. Arrowheads point to pigments in the keratinocytes. Melan-A and S100 stains highlights scattered melanocytes in the dermal epidermal junction. Scale bar, 30 µM.
Figure 20:
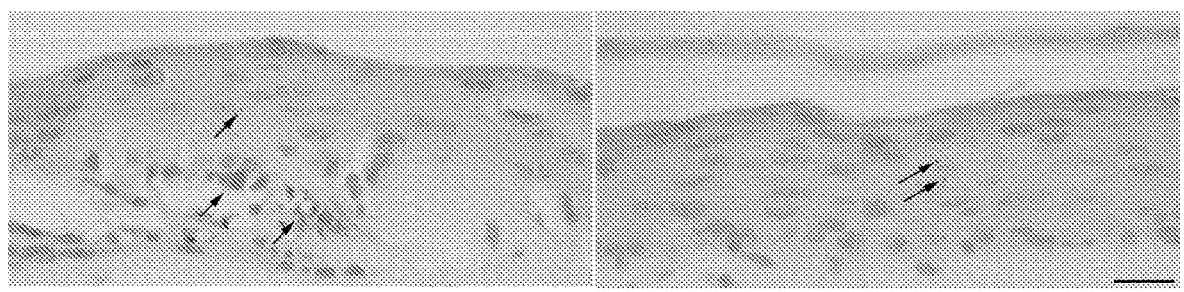
FIG. 20. hiMel derived from human fetal fibroblast pigment production in response to MSH stimulation. 30 skin equivalents were constructed using foreskin keratinocytes and hiMels. a-MSH was applied on top of the epidermis. The skin reconstructed was harvested 3 weeks after a-MSH stimulation. Fontana-Mason staining of the a-MSH-treated (left panel) and control (right panel) 30 skin reconstructs. Arrow heads point to pigments. Scale bar, 30 µm.

To study the biological functions of hiMels, we generated 3D organotypic skin equivalents using hiMels, parental fetal fibroblasts and foreskin keratinocytes as previously described (16). Melan-A and S100 positive melanocytes located near the dermal-epidermal junction (FIG. 19). Fontana-Masson staining showed melanin pigment in the basal and supra-basal layer keratinocytes, indicating that the iMels not only produce pigment and but also transfer pigment to surrounding keratinocytes (FIG. 19). In addition, we found that melanin production in hiMels-constituted 3D skin reconstruct increased upon a-MSH stimulation (FIG. 20).

Figure 21A:
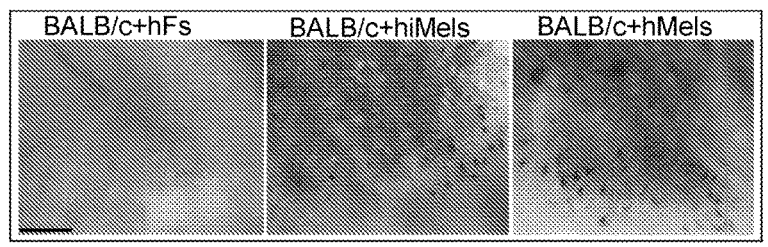
Figure 21B:
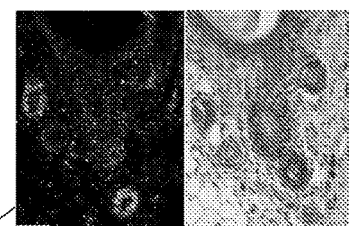
Figure 21C:
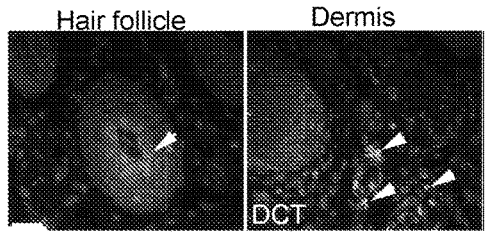
Figure 21D:
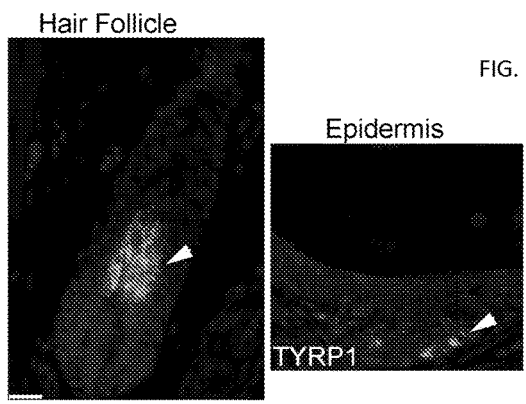
Figure 21D:
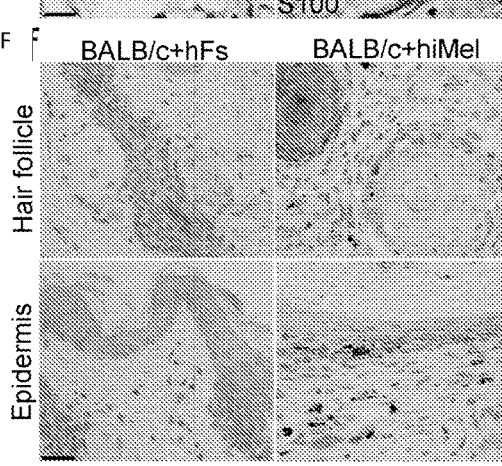

To investigate the in vivo function of hiMels, we developed a novel assay to assess skin and hair pigmentation using a modified hair patch assay (34). In this assay, hiMels were mixed with epithelial cells and dermal fibroblasts derived from neonatal BALB/c albino mouse skin and then transplanted into the back skin of nude mice. Human normal skin melanocytes were used as positive controls. When human normal skin melanocytes or hiMels were mixed with cells prepared from BALB/c albino mouse skin, pigmented hair follicles formed (FIG. 21a, middle and right panels). To avoid the possibility of contaminating melanocytes or melanocyte stem cells in the parental fibroblasts, we mixed parental fibroblasts with BALB/c-derived epithelial cells and dermal fibroblasts and then transplanted the cell mixture into the back skin of nude mice. Only white hair was produced under these conditions (FIG. 21a, left panel). The grafts were harvested and histologic examination revealed epidermal lined cysts with many hair follicles (FIG. 21b). We found that hiMels specifically recognized by FITC labeled human-specific Alu-probe, were localized near the dermal-epidermal junction, inside the hair follicles (FIG. 21b) and in the dermis (data not shown) in the pigmented grafts. DCT+ cells can be seen in the interfollicular dermis and bulb region of hair follicles (FIG. 21c). Meanwhile, TYRP1+ cells were observed in hair follicles and the epidermis (FIG. 21d). Similarly, S100+ cells were seen near the dermal-epidermal junction in the epidermis and in the hair follicles (FIG. 21e). Some of the melanocytes were also localized in the dermis. We then performed Fontana-Masson staining to study the distribution of melanin pigment in the epidermis and hair follicles. Melanin pigment was detected in the epidermis, hair follicle epithelium and hair shafts (FIG. 21f), indicating that the hiMels were able to transfer pigment to the surrounding keratinocytes in vivo (FIG. 21O. The pigmentation patterns in the hair patch assays using hiMels were identical to those of normal skin melanocytes. We did not find any melanin pigment in the hair patch assays using parental fibroblasts and BALB/c-derived cells (FIG. 21O. These data indicate that hiMels are functionally identical to normal skin melanocytes.

Figure 22A:
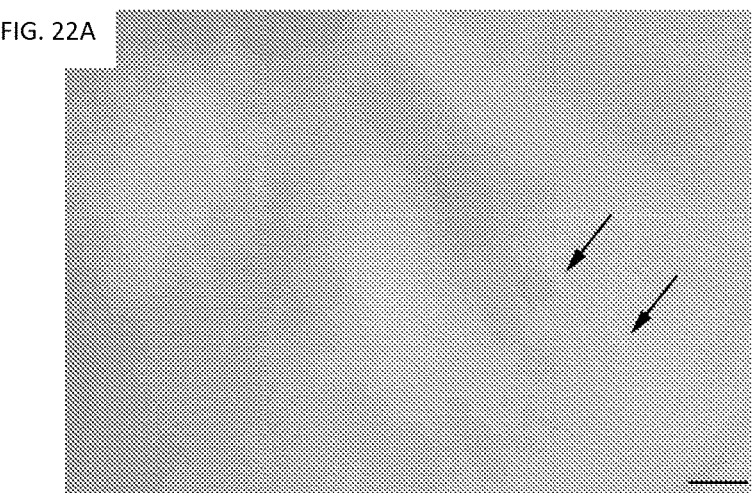
FIGS. 22A-22B. Skin reconstitution assays using MITF-induced fibroblasts. P2 human fetal fibroblasts were infected with MITF and cultured for 50 days. These MITF induced cells were used in the skin reconstitution assays.
Figure 22B:
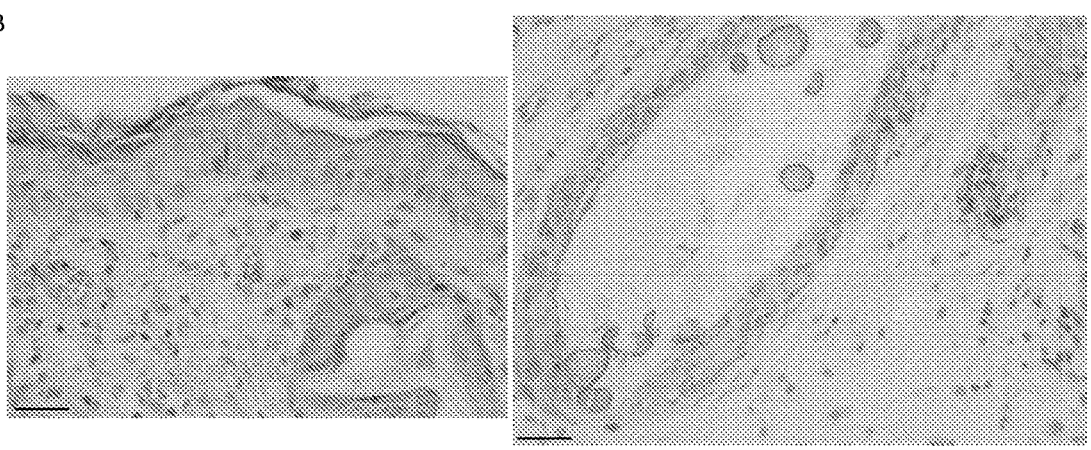

To test whether MITF alone is sufficient to generate functional melanocytes in vivo, we cultured MITF-infected fibroblasts for 50 days in the melanocyte inducing medium. We then transplanted MITF-infected fibroblasts with BALB/c-derived epithelial cells and dermal fibroblasts mixture into mouse back skin. We did not find any pigment in the hair follicles and epidermis in the skin reconstruct (FIGS. 22a and 22b), indicating that MITF alone is insufficient to induce melanocytes from fibroblasts.

Figure 23:
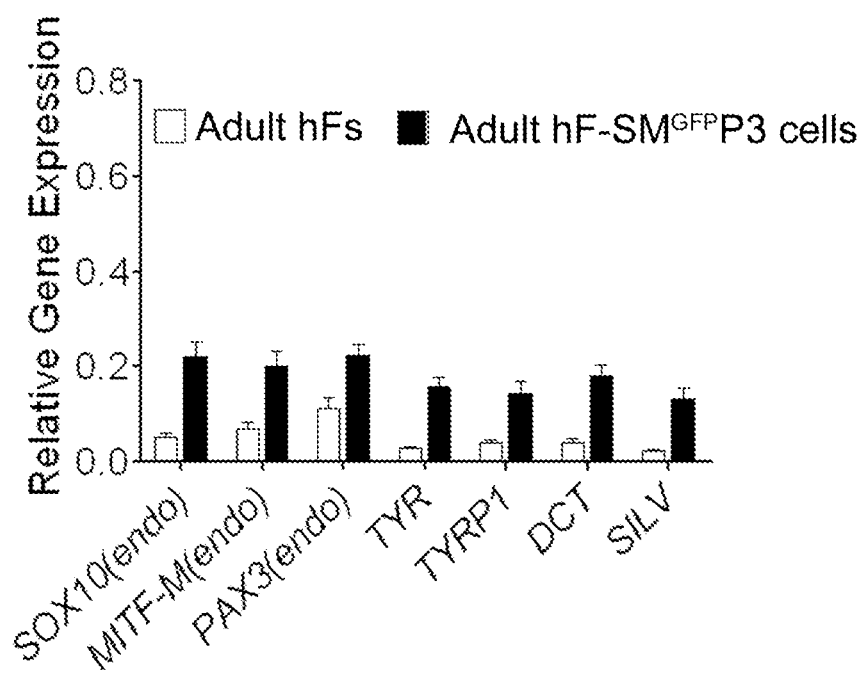
FIG. 23. qRT-PCR analysis of melanocytic markers in human adult fibroblasts (adult hFs) and SMGFPP3 infected adult hFs (adult hf-SMGFPP3 cells). Adult hF-SMGFPP3 cells were cultured for 15 days under selection of G418 and sorted for qRT-PCR analysis. The melanocytic markers included MITF (endo), TYR, TYRP1, OCT, P, SOX10 (endo) and PAX3 (endo). Data shown are mean±SD of the expression from three independent experiments.
Figure 24A:
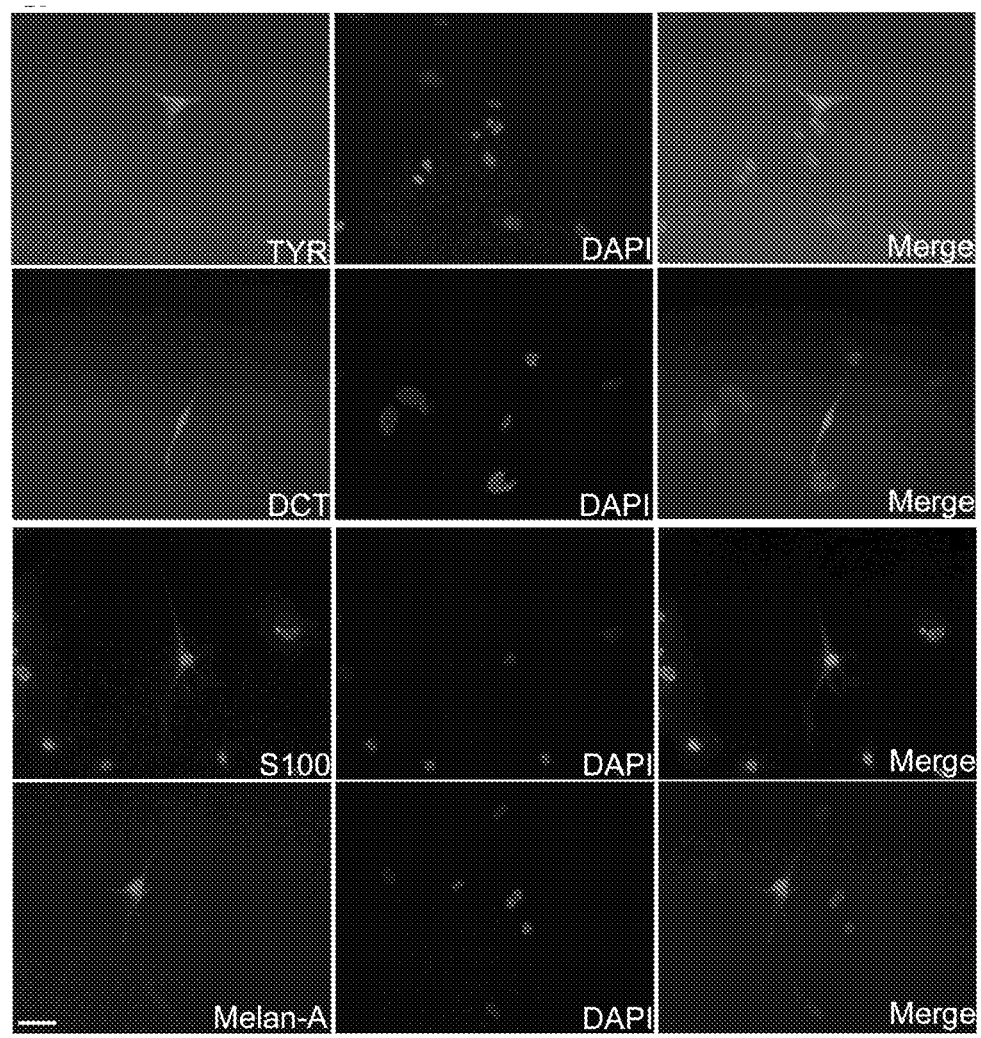
FIGS. 24A-24B. lmmunostaining analysis of TYR, DCT, S100 and Melan-A in SMGFPP3 infected human adult fibroblasts (adult hFs).
Figure 24B:
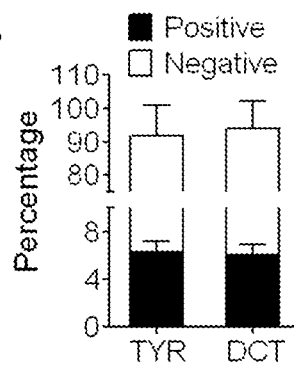
Figure 25:
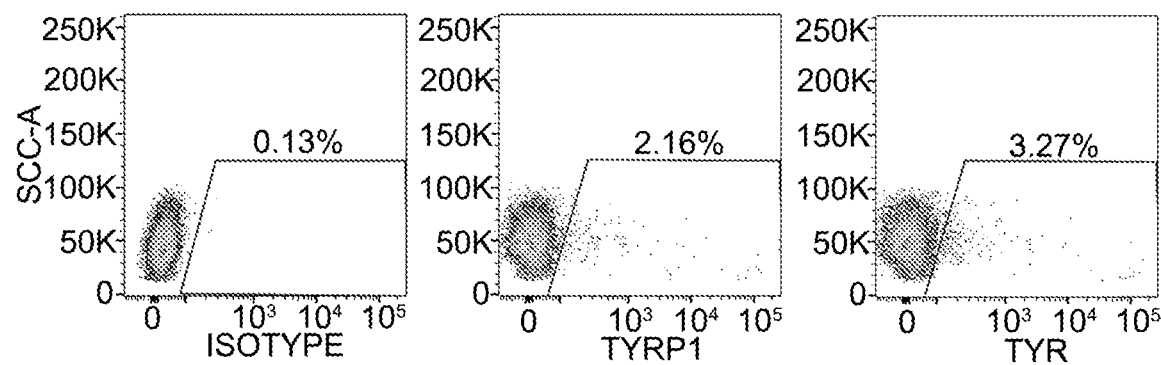
FIG. 25. Flow cytometry analysis of the percentage of TYR+ and TYRP1+ cells in SMGFPP3 reprogrammed adult hFs. Representative data are from 3 independent experiments.

We then used the same procedure to human adult fibroblasts (adult hFs) and infected them with the SMGFPP3 virus combination. The SMGFPP3-infected cells were cultured for 15 days, and GFP+ cells were sorted and cultured in melanocyte inducing medium for 40 days. qRT-PCR analysis of the GFP+ cells showed that the melanocytic network for melanin production and transfer was indeed activated (FIG. 23). We also detected expression of key melanocytic markers and found that cells with typical melanocyte morphology expressed TYR, DCT, S100 and Melan-A (FIG. 24a). Notably, only 6% of the adult hFs expressed melanocytic markers indicating that the adult fibroblast reprogramming efficiency was much lower than that for fetal fibroblasts (FIG. 24b). We performed flow cytometric analysis to measure the percentage of the TYR+ and TYRP1+ cells in the adult reprogrammed cells and found only 3.27% and 2.16%, respectively (FIG. 25).

DISCUSSION

We developed a novel method to generate melanocytes directly from fibroblasts. This process is call direct reprogramming or trans-differentiation. It is distinctively different from generating induced pluripotent stem cells (iPSCs) and then differentiating iPSCs to melanocytes. iPSCs take a long time to generate and undifferentiated iPSCs that are tumorigenic may contaminate the differentiated cells and differentiation efficiency is low. The process we developed is much more efficient and distinctively different. Normal fibroblasts were infected/transfected with plasmids containing Pax3, Sox10 and Mitf. The cells were then cultured in the melanocyte culture medium. Several weeks later, melanocytes emerged in the culture. The induced melanocytes have typical foreskin derived melanocyte morphology, express all the markers as melanocytes by gene expression analysis or immunohistochemistry and are positive by Fontana-Mason staining. When the induced melanocytes are included in the 3D skin equivalent culture, the melanocytes migrated to dermal epidermal junction as normal melanocytes and transferred melanin to keratinocytes. Therefore, these cells have phenotypes and function as normal melanocytes.

In translational medicine, generation of functional melanocytes by direct reprogramming establishes a means for obtaining a scalable source of autologous melanocytes, which then can be used for developing cell-based treatments for pigmentary disorders such as vitiligo and hypopigmentation associated with congenital disorders. Reprogramming fibroblasts to melanocytes specifically from patients with melanoma also serves as a powerful strategy for studying the etiology of melanoma.

Example 2

Treatment of Vitiligo

A patient with stable vitiligo presents in the clinic for treatment. The depigmented area is more than 5 cm in greatest dimension. The lesion is stable for the past 6-12 months. A 3 mm biopsy will be taken from patient's arm and fibroblasts isolated from the biopsy. Several approaches can be employed to generate cells expressing the transcription factors described in Example 1. The fibroblasts can be transfected with vectors containing MITF, Sox10 and Pax3, synthetic mRNAs of these 3 factors, or proteins directly injected into cells. Any approach that gives rise to sufficient levels of protein expression of these three factors is encompassed by the present invention. After transfection, these fibroblasts will be cultured in the medium described above for 25-40 days. We will then measure the percentage of melanocytes in the culture using FACS or immunohistochemistry. The resultant cells will be suspended in a medium or seeded onto a biocompatible membrane. The epidermis in the area with vitiligo will be removed using a mechanical method (e.g., abrasion) or laser method. The melanocytes will then be applied to the area with vitiligo. The area is then covered with bandage and the epidermis will heal with color. In preferred embodiments, the epidermis heals with color in 1-2 weeks.

Example 3

Screening Therapeutic Agents for the Treatment of Disease Using the Melanocytes of the Invention The present invention provides a new approach for screening small molecules for the treatment of a variety of disorders. For example, fibroblasts from a patient with p16 loss can be obtained. The fibroblasts will be reprogrammed to melanocytes as described above in Example 1. The melanocytes so generated can then be incubated in the presence and absence of a test agent. Agents which inhibit malignant transformation of these cells following exposure to UV radiation should have efficacy for the treatment of such disorders.

Example 4

In an approach to delay or prevent hair graying, fibroblasts from elderly patients can be obtained. The fibroblasts will be reprogrammed to melanocytes as described above. These melanocytes will be used to screen for small molecules that prevent of delay melanocyte aging. Molecules so identified can be used to advantage to prevent or treat hair graying.

REFERENCES

1. Caiazzo, M. et al. Direct generation of functional dopaminergic neurons from mouse and human fibroblasts. Nature 476, 224-227 (2011).
2. Huang, P. et al. Induction of functional hepatocyte-like cells from mouse fibroblasts by defined factors. Nature 475, 386-389 (2011).
3. Ieda, M. et al. Direct reprogramming of fibroblasts into functional cardiomyocytes by defined factors. Cell 142, 375-386 (2010).
4. Pang, Z. P. et al. Induction of human neuronal cells by defined transcription factors. Nature 476, 220-223 (2011).
5. Qian, L. et al. In vivo reprogramming of murine cardiac fibroblasts into induced cardiomyocytes. Nature 485, 593-598 (2012).
6. Sekiya, S. & Suzuki, A. Direct conversion of mouse fibroblasts to hepatocyte-like cells by defined factors. Nature 475, 390-393 (2011).
7. Song, K. et al. Heart repair by reprogramming non-myocytes with cardiac transcription factors. Nature 485, 599-604 (2012).
8. Vierbuchen, T. et al. Direct conversion of fibroblasts to functional neurons by defined factors. Nature 463, 1035-1041 (2010).
9. Du, P., Kibbe, W. A. & Lin, S. M. lumi: a pipeline for processing Illumina microarray. Bioinformatics 24, 1547-1548 (2008).
10. Smyth, G. K. Linear models and empirical bayes methods for assessing differential expression in microarray experiments. Stat Appl Genet Mol Biol 3, Article 3 (2004).
11. Smyth, G. K. (ed.) in Bioinformatics and Computational Biology Solutions using R and Bioconductor. (Springer, New York; 2005).
12. Prouty, S. M., Lawrence, L. & Stenn, K. S. Fibroblast-dependent induction of a murine skin lesion with similarity to human common blue nevus. Am J Pathol 148, 1871-1885 (1996).
13. Benjamini, Y. H., Y Controlling the false discovery rate: a practical and powerful approach to multiple testing. Journal of the Royal Statistical Society. Series B 57 (1995).
14. Subramanian, A. et al. Gene set enrichment analysis: a knowledge-based approach for interpreting genome-wide expression profiles. Proc Natl Acad Sci USA 102, 15545-15550 (2005).

15. Tropepe, V. et al. Retinal stem cells in the adult mammalian eye. Science 287, 2032-2036 (2000).
16. Li, L., Fukunaga-Kalabis, M. & Herlyn, M. The three-dimensional human skin reconstruct model: a tool to study normal skin and melanoma progression. J Vis Exp (2011).
17. Zheng, Y. et al. Organogenesis from dissociated cells: generation of mature cycling hair follicles from skin-derived cells. J Invest Dermatol 124, 867-876 (2005).
18. Zheng, Y. et al. Mature hair follicles generated from dissociated cells: a universal mechanism of folliculoneogenesis. Dev Dyn 239, 2619-2626 (2010).
19. Lichti, U. et al. In vivo regulation of murine hair growth: insights from grafting defined cell populations onto nude mice. J Invest Dermatol 101, 124S-129S (1993).
20. Weinberg, W. C. et al. Reconstitution of hair follicle development in vivo: determination of follicle formation, hair growth, and hair quality by dermal cells. J Invest Dermatol 100, 229-236 (1993).
21. Tachibana, M. et al. Ectopic expression of MITF, a gene for Waardenburg syndrome type 2, converts fibroblasts to cells with melanocyte characteristics. Nat Genet 14, 50-54 (1996).
22. Adameyko, I. et al. Sox2 and Mitf cross-regulatory interactions consolidate progenitor and melanocyte lineages in the cranial neural crest. Development 139, 397-410 (2012).
23. Southard-Smith, E. M., Kos, L. & Pavan, W. J. S ox10 mutation disrupts neural crest development in Dom Hirschsprung mouse model. Nat Genet 18, 60-64 (1998).
24. Hornyak, T. J., Hayes, D. J., Chiu, L. Y. & Ziff, E. B. Transcription factors in melanocyte development: distinct roles for Pax-3 and Mitf. Mech Dev 101, 47-59 (2001).
25. Galibert, M. D., Yavuzer, U., Dexter, T. J. & Goding, C. R. Pax3 and regulation of the melanocyte-specific tyrosinase-related protein-1 promoter. J Biol Chem 274, 26894-26900 (1999).
26. Baumer, N. et al. Retinal pigmented epithelium determination requires the redundant activities of Pax2 and Pax6. Development 130, 2903-2915 (2003).
27. Saito, H. et al. Melanocyte-specific microphthalmia-associated transcription factor isoform activates its own gene promoter through physical interaction with lymphoid-enhancing factor 1. J Biol Chem 277, 28787-28794 (2002).
28. Prince, S., Wiggins, T., Hulley, P. A. & Kidson, S. H. Stimulation of melanogenesis by tetradecanoylphorbol 13-acetate (TPA) in mouse melanocytes and neural crest cells. Pigment Cell Res 16, 26-34 (2003).
29. Curran, K. et al. Interplay between Foxd3 and Mitf regulates cell fate plasticity in the zebrafish neural crest. Dev Biol 344, 107-118 (2010).
30. Dankort, D. et al. Braf(V600E) cooperates with Pten loss to induce metastatic melanoma. Nat Genet 41, 544-552 (2009).
31. Sviderskaya, E. V. et al. Complementation of hypopigmentation in p-mutant (pink-eyed dilution) mouse melanocytes by normal human P cDNA, and defective complementation by OCA2 mutant sequences. J Invest Dermatol 108, 30-34 (1997).
32. Mili, S., Moissoglu, K. & Macara, I. G. Genome-wide screen reveals APC-associated RNAs enriched in cell protrusions. Nature 453, 115-119 (2008).
33. Collins, C. A., Kretzschmar, K. & Watt, F. M. Reprogramming adult dermis to a neonatal state through epidermal activation of beta-catenin. Development 138, 5189-5199 (2011).
34. Morris, R. J. et al. Capturing and profiling adult hair follicle stem cells. Nat Biotechnol 22, 411-417 (2004).
35. Pfisterer, U. et al. Direct conversion of human fibroblasts to dopaminergic neurons. Proc Natl Acad Sci USA 108, 10343-10348 (2011).
36. Li, L. et al. Human dermal stem cells differentiate into functional epidermal melanocytes. J Cell Sci 123, 853-860 (2010).

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A method for producing melanocytes comprising:
   a) providing fibroblast cells capable of transdifferentiation into melanocytes;
   b) culturing said fibroblast cells in melanocyte culture medium for transdifferentiation;
   c) introducing nucleic acids encoding each of at least microphthalmia-associated transcription factor (MITF), and SRY-related HMG-box (SOX10) transcription factors and, optionally a nucleic acid encoding paired box-3 (PAX-3) transcription factor, into said cells, wherein said transcription factors are expressed to cause transdifferentiation into melanocytes expressing melanocyte markers TYR, DCT, S-100 and Melan-A; and, optionally
   d) isolating said melanocytes.

2. The method of claim 1, wherein nucleic acid encoding all three transcription factors are introduced.

3. The method of claim 1, wherein said cells are mammalian in origin.

4. The method of claim 3, wherein said cells are human in origin.

5. The method of claim 2, wherein said fibroblast cells are fetal or adult fibroblasts.

6. The method of claim 1, wherein said transcription factors are encoded by one or more recombinant expression vectors.

7. The method of claim 1, wherein said nucleic acid is synthetic mRNA.

8. The method of claim 1, where is said culture media comprises Dulbecco's modified Eagle medium, fetal bovine serum, non-essential amino acids, sodium pyruvate and penicillin/streptomycin.

9. The method of claim 1, wherein said fibroblasts cells are obtained from a patient in need of treatment with melanocytes.

* * * * *